(12) United States Patent
Nishiuchi et al.

(10) Patent No.: US 8,970,138 B2
(45) Date of Patent: Mar. 3, 2015

(54) PARTICLE BEAM IRRADIATION SYSTEM AND METHOD FOR OPERATING THE SAME

(71) Applicant: Hitachi, Ltd., Tokyo (JP)

(72) Inventors: Hideaki Nishiuchi, Tokyo (JP); Koji Tobinaga, Hitachi (JP); Kunio Moriyama, Tokyo (JP); Takuya Nomura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/333,809

(22) Filed: Jul. 17, 2014

(65) Prior Publication Data

US 2015/0031931 A1 Jan. 29, 2015

(30) Foreign Application Priority Data

Jul. 26, 2013 (JP) ................ 2013-155770

(51) Int. Cl.
*H05H 13/04* (2006.01)
*A61N 5/10* (2006.01)
(52) U.S. Cl.
CPC ....... *A61N 5/1067* (2013.01); *A61N 2005/1074* (2013.01); *A61N 2005/1087* (2013.01)
USPC ................ 315/503; 250/396 ML; 250/396 R
(58) Field of Classification Search
None
See application file for complete search history.

(56) References Cited

U.S. PATENT DOCUMENTS

| | | | | |
|---|---|---|---|---|
| 5,177,448 A | * | 1/1993 | Ikeguchi et al. | 315/503 |
| 5,483,129 A | * | 1/1996 | Yamamoto | 315/503 |
| 5,698,954 A | * | 12/1997 | Hirota et al. | 315/503 |
| 6,265,837 B1 | * | 7/2001 | Akiyama et al. | 315/503 |
| 6,670,618 B1 | * | 12/2003 | Hartmann et al. | 250/491.1 |
| 6,897,451 B2 | * | 5/2005 | Kaercher et al. | 250/396 R |
| 7,274,018 B2 | * | 9/2007 | Adamec et al. | 250/310 |
| 7,939,809 B2 | * | 5/2011 | Balakin | 250/396 R |
| 8,188,688 B2 | * | 5/2012 | Balakin | 315/503 |
| 8,253,113 B2 | * | 8/2012 | Nishiuchi et al. | 250/396 R |
| 2008/0191142 A1 | * | 8/2008 | Pedroni | 250/396 ML |

FOREIGN PATENT DOCUMENTS

| | | |
|---|---|---|
| JP | 07-303710 A | 11/1995 |
| JP | 2921433 A | 7/1999 |

(Continued)

OTHER PUBLICATIONS

Iwata et al., "Multiple-energy operation with extended flattops at HIMAC", Nuclear Instruments and Methods in Physics Research A, Sep. 2010, vol. 624, pp. 33-38.

(Continued)

*Primary Examiner* — Crystal L Hammond
(74) *Attorney, Agent, or Firm* — Mattingly & Malur, PC

(57) ABSTRACT

A control data about the devices constituting the synchrotron are formed by an initial acceleration control data item, a plural extraction control data items, a plural energy change control data items connecting the plural extraction control data items, and a plural deceleration control data items corresponding to the plural extraction control data items. An affected part position detection unit and an extraction permission determination unit are provided to determine whether the position of a marker shown in transparent image information is included within a beam irradiation permission range. If the marker position is found included, the extraction permission determination unit outputs to an interlock system an extraction permission determination signal permitting beam extraction.

14 Claims, 10 Drawing Sheets

(56) References Cited

FOREIGN PATENT DOCUMENTS

| | | |
|---|---|---|
| JP | 2008-226740 A | 9/2008 |
| JP | 2011-124149 A | 6/2011 |
| JP | 4873563 B2 | 2/2012 |
| JP | 2013-111406 A | 6/2013 |
| JP | 2014-22222 A | 2/2014 |
| JP | 2014-28061 A | 2/2014 |

OTHER PUBLICATIONS

Nishiuchi, U.S. Appl. No. 14/163,143, filed Jan. 24, 2014, Unpublished.

* cited by examiner

PRIOR ART

PARTICLE BEAM IRRADIATION SYSTEM AND METHOD FOR OPERATING THE SAME

BACKGROUND OF THE INVENTION

The present invention relates to a particle beam irradiation system suitable for a particle beam treatment making use of a charged particle beam (ion beam) of protons or heavy ions. More particularly, the invention relates to a particle beam irradiation system capable of controlling changes in beam energy and realizing operation cycle updates in a short time, and to a method for operating the system.

The particle beam treatment is known as cancer radiotherapy whereby the affected part of a patient with a cancer is irradiated with an ion beam of protons or heavy ions for treatment. One method of ion beam irradiation is a scanning irradiation method.

Where a synchrotron is adopted as an ion beam generator for controlling changes in beam energy as required of the scanning irradiation method as a method for providing the control in a short time, there is available a multistage extraction control operation for bringing about irradiation with an ion beam at a plural energy stages within one operation cycle of the ion synchrotron, as disclosed in Japanese Patent No. 4873563, JP-2011-124149-A, and "Nuclear Instruments and Methods in Physics Research," No. A624 (September 2010), pp. 33-38 (hereinafter, referred to as Non-patent Document 1).

Japanese Patent No. 2921433 and JP-2013-111406-A describe methods for irradiating with a beam a respiratory moving organ of which the affected part moves over time due to the patient's physiological activities such as respiration.

SUMMARY OF THE INVENTION

With the scanning irradiation method, the control of irradiation aimed at an irradiation field (referred to as the layer hereunder) in the depth direction of the affected part is implemented by controlling the energy of an irradiation ion beam. For this reason, it is necessary to bring about rapidly the changes in the energy of the ion beam supplied from the ion beam generator in order to enhance the dose rate in effect when the irradiation scanning method is applied. Also with the scanning irradiation method, it is necessary to control the energy of beam irradiation in accordance with the tumor volume (depth from the body surface). This requires suitably controlling the combination of irradiation beam energy stages with regard to each patient or each affected part to be irradiated.

Where the synchrotron is adopted as the ion beam generator, a series of operations such as injection, acceleration, extraction and deceleration are controlled as one operation cycle. Where control of the changes in ion beam energy is performed repeatedly as in the case of the scanning irradiation method, the synchrotron needs to have the operation cycle updated every time, so that it takes time to change the ion beam energy. As a countermeasure against this problem, Japanese Patent No. 4873563 and Non-patent Document 1 describe the multistage extraction operation whereby the beam is extracted at the plural energy stages within one operation cycle. For example, Non-patent Document 1 shows that the affected part can be irradiated with the beam at all energy stages in one round of operation control when there is prepared operation control data that integrates into one range all energy ranges available for irradiation by the synchrotron and when the beam is extracted by extending the flat top period only with the energy for beam irradiation. Further, since the beam is available for irradiation at all energy stages in one round of operation control, the synchrotron can always implement irradiation by use of the same operation control data. This provides the advantageous effect of simplifying the operation control of the synchrotron in a particle beam treatment system.

However, to implement operation control effectively, as described in Japanese Patent No. 4873563 and Non-patent Document 1, requires that the amount of accumulated beam charge of the synchrotron be sufficient for irradiating the affected part with the entire energy for irradiation in one operation cycle.

For example, if for some reason the amount of accumulated beam charge necessary for treatment irradiation is not available under acceleration control of the synchrotron, the accumulated beam charge will be exhausted halfway through a preset irradiation energy range. If the accumulated beam charge in the synchrotron is exhausted, it is necessary to interrupt ion beam irradiation for the sake of transition from extraction control to deceleration control in order to update the operation control of the synchrotron. Where use is made of the operation control data that integrates into one range all energy ranges available for irradiation by the synchrotron, direct transition from extraction control at the extraction energy to deceleration control cannot be made because of the need to ensure the continuity of set values. For this reason, the energy change control data ranging from extraction control at the extraction energy to deceleration control needs to be updated. The time required to perform the transition from extraction control at the extraction energy to deceleration control is one factor that lowers the dose rate and makes it difficult to shorten treatment time. Likewise, direct transition from extraction control at the extraction energy to deceleration control cannot be performed when ion beam irradiation is interrupted due to a failure in the component devices making up the particle beam treatment system.

Where use is made of the operation control data that integrates into one range all energy ranges available for irradiation by the synchrotron and where irradiation conditions are in effect involving a narrow absorbed dose range fit for the thickness of the affected part (called the Spread-Out Bragg Peak, abbreviated to SOBP hereunder), there is a tendency that it takes a longer time to perform controls ranging from injection beam energy to irradiation start energy and from irradiation end energy to deceleration end energy on the synchrotron, which amounts to a wasteful time not contributing to beam irradiation, as compared with the time required for beam irradiation. This is another factor that lowers the dose rate and makes it difficult to shorten treatment time. Since the SOBP varies with each patient and with each affected part, it is necessary to select the irradiation energy stage needed to form a suitable SOBP as synchrotron operation control data and to control the updates of the operation control data reflecting the selected irradiation energy.

JP-2011-124149-A describes a controller of an accelerator equipped with a magnetic field reference generation unit that outputs information on magnetic flux density corresponding to elapsed time with reference to a coil current which excites a magnetic field coil of the accelerator, and a current reference conversion unit that obtains a coil current which generates the magnetic field corresponding to the magnetic flux density information. The magnetic flux density information output by the magnetic field reference generation unit is then output in a combination of four patterns (initial rise pattern, decrease pattern, increase pattern, and completion pattern) by a control method that implements beam extraction at the plural energy stages within one operation cycle. According to JP-2011-

124149-A, ion beam extraction is made available at the plural energy stages in one operation cycle by suitably combining the four magnetic flux density patterns. On the basis of this feature, it is possible to select an irradiation energy stage necessary for forming an appropriate SOBP. On the other hand, the timings for selecting and outputting the four patterns are written beforehand in a timing controller so that, as in the case of Japanese Patent No. 4873563 and Non-patent Document 1, direct transition from extraction control at the extraction energy to deceleration control cannot be performed when ion beam irradiation is interrupted. The problem still remains that unless the energy change control data ranging from extraction control at the extraction energy to deceleration control is updated, the transition to deceleration control (referred to as the completion pattern in JP-2011-124149-A) cannot be performed.

Also, where the scanning irradiation method is applied to respiratory moving organs, control is required so that irradiation is performed when the affected part is detected to have moved due to the patient's physiological activities and the position of beam irradiation is found included in a radiation range of the affected part. In this case, the synchrotron is arranged to perform beam extraction control upon output of an extraction permission control signal indicating that the beam irradiation position is included in the radiation range of the affected part and upon completion of the setting of the extraction conditions on the synchrotron. This arrangement helps improve the accuracy of beam irradiation aimed at the respiratory moving organs. That is, when the beam is extracted from the synchrotron on the basis of the extraction permission control signal, the precision of beam irradiation directed at the respiratory moving organs can be enhanced.

When the beam is extracted from the synchrotron on the basis of the extraction permission control signal under control of such beam irradiation aimed at a respiratory moving organ, the synchrotron is transitioned to deceleration control the moment the output of the extraction permission control signal is stopped, and the beam acceleration and extraction conditions necessary for the next stage of irradiation are set successively, as discussed in Japanese Patent No. 2921433. When transition is made to deceleration control as soon as the output of the extraction permission control signal is stopped, deceleration is started even if there remains the beam circulating inside the synchrotron. This poses the problem of low efficiency of the use of the beam circulating within the synchrotron.

JP-2013-111406-A shows that transition to deceleration control is not performed the moment the output of the extraction permission control signal is stopped, unlike in the case of Japanese Patent No. 2921433 having to deal with this problem, so as to improve the efficiency of the use of the beam circulating in the synchrotron by maintaining operation control with the beam extraction control stopped during a predetermined waiting time. It is shown that if the extraction permission control signal is again output during the waiting time, beam extraction control is performed to boost the efficiency of the use of the beam circulating inside the synchrotron.

However, where the beam is extracted from the synchrotron on the basis of the extraction permission control signal during a multistage extraction control operation, even if beam extraction control is stopped for transition to waiting control by stopping the output of the extraction permission control signal as discussed in JP-2013-111406-A, it is necessary to perform transition to deceleration control when the predetermined waiting time is exceeded. It is thus not shown how to implement energy change control as demanded in the multistage extraction control operation.

Furthermore, upon transition to deceleration control when the beam circulating inside the synchrotron is not sufficient, direct transition cannot be made from extraction control at the extraction energy to deceleration control if ion beam irradiation is interrupted, as in the case of Japanese Patent No. 4873563, JP-2011-124149-A and Non-patent Document 1. The problem still remains that transition to deceleration control is not available unless the energy change control data ranging from extraction control at the extraction energy to deceleration control is updated.

It is therefore an object of the present invention is to provide a particle beam irradiation system and a method for operating the system whereby beam irradiation is performed over a desired energy range in a short operation cycle during a multistage extraction control operation for implementing the control of changes in the energy of the beam extracted from the synchrotron, so that the dose rate will be improved.

Another object of the present invention is to provide a particle beam irradiation system and a method for operating the system whereby the operation cycle is updated in a short time upon interruption of ion beam irradiation during a multistage extraction control operation for implementing the control of changes in the energy of the beam extracted from the synchrotron, so that the dose rate will be improved.

A further object of the present invention is to provide a particle beam irradiation system and a method for operating the system whereby control is implemented to give irradiation when movements of the affected part due to the patient's physiological activities are detected and the position of beam irradiation is found included in the radiation range of the affected part, so that the dose rate and the accuracy of beam irradiation will be improved.

In order to solve the above problems, for example, to adopt a structure described in the scope of the appended claims.

The present invention includes a plural means for solving the above problems, but if the one example, a charged particle beam irradiation system including: a synchrotron accelerating an ion beam and having the accelerated ion beam extracted therefrom; an irradiation device for executing irradiation with the ion beam extracted from the synchrotron; a detection unit for detecting a movement of an affected part of a patient caused by physiological activities of the patient; an extraction permission determination unit for outputting an extraction permission determination signal on the basis of an output value from the detection unit; and a controller for causing operation control data about component devices making up the synchrotron to be formed by at least one initial acceleration control data item, a plural extraction control data items for ion beam extraction at the plural energy stages, a plural energy change control data items connecting the plural extraction control data items, and a plural deceleration control data items corresponding to the plural extraction control data items, the controller further combining the control data items to provide beam extraction control at the plural energy stages. The controller performs control of beam extraction from the synchrotron on the basis of the extraction permission determination signal output from the extraction permission determination unit.

With this structure, it is possible rapidly to perform control of changes in the energy of the beam extracted from the synchrotron. Because rapid transition to deceleration control is available from any energy stage during the multistage extraction control operation, the operation cycle can be updated in a short time if irradiation with the ion beam is interrupted, so that the dose rate is improved and treatment time is shortened. Furthermore, when control is performed to extract the beam from the synchrotron on the basis of the extraction permission determination signal, the accuracy of irradiating a respiratory moving organ with the beam is enhanced.

The present invention may be configured more specifically as follows:

Preferably, upon control of extraction of the beam from the synchrotron, the controller may perform control of beam extraction a number of times at the same energy stage on the basis of the extraction permission determination signal output from the extraction permission determination unit.

Preferably, the extraction permission determination unit may output the extraction permission determination signal if the detection unit detects that the affected part is within an extraction permission range, the extraction permission determination unit not outputting the extraction permission determination signal if the detection unit detects that the affected part is not within the extraction permission range.

With this structure, even if beam irradiation is interrupted upon detection of movements of the affected part caused by the patient's physiological activities, beam irradiation can be resumed at the same energy stage for efficient execution of beam irradiation.

Preferably, the controller may include a timing system for outputting a plural control timing signals for managing control timings of the component devices making up the synchrotron, and a power supply controller for controlling the component devices making up the synchrotron. The initial acceleration control data item, the plural extraction control data items, the plural energy change control data items, and the plural deceleration control data items forming the operation control data may be stored in the power supply controller. The power supply controller may input the plural control timing signals output from the timing system and, on the basis of the plural control timing signals, update selectively the initial acceleration control data item, the plural extraction control data items, the plural energy change control data items, and the plural deceleration control data items.

Preferably, the charged particle beam irradiation system may further include a beam amount detection unit for detecting the amount of the beam accumulated in the synchrotron. Given the input of the extraction permission determination signal output from the extraction permission determination unit, the controller may set extraction conditions for operation control of the synchrotron, the controller further issuing a command to perform beam extraction control upon input of the extraction permission determination signal. If the extraction permission determination signal is stopped, the controller may determine whether to wait to permit beam extraction at the current energy stage when the extraction permission determination signal is again output, to make transition to energy change control so as to permit beam irradiation at the next energy stage, or to make transition to deceleration control in accordance with the detected amount of the beam accumulated in the synchrotron by the beam amount detection unit and with the result of a determination of whether beam irradiation at the current energy stage has been completed, the controller further outputting to the timing system a control command corresponding to the control determined earlier.

Preferably, the controller further include an interlock system that outputs an initial acceleration command to accelerate beam energy injected into the synchrotron up to an initial extraction energy stage for beam extraction, an irradiation preparation start command to set extraction conditions following initial acceleration or energy change with the synchrotron, an irradiation wait command to indicate that the setting of the extraction conditions is completed on the synchrotron, a beam extraction command to be output in accordance with the extraction permission determination signal output from the extraction permission determination unit and with status of the extraction conditions set on the synchrotron, an irradiation stop command to stop beam irradiation aimed at the affected part, an energy change command to be output on the basis of irradiation progress information about the ion beam with which the patient has been irradiated, a deceleration control command to be output on the basis of status of the component devices making up the charged particle beam irradiation system including the synchrotron and the irradiation device, and an irradiation complete command to indicate that the irradiation is completed. The timing system may selectively output the corresponding one of the plural control timing signals on the basis of the initial acceleration command, the irradiation preparation start command, the irradiation wait command, the irradiation stop command, the energy change command, and the deceleration control command output from the interlock system.

Preferably, given the timing signal for starting deceleration control from among the timing signals input from the timing system, the power supply controller may select one of the plural deceleration control data items which corresponds to the energy stage in effect upon completion of irradiation control, the power supply controller further performing control to make transition to deceleration control.

With this structure, upon interruption of ion beam irradiation because of an insufficient amount of the beam accumulated inside the synchrotron, direct transition is made to deceleration control so that the operation cycle can be updated in a short time.

Preferably, the interlock system may further output the deceleration control command if a failure has occurred in any one of the component devices making up the charged particle beam irradiation system including the synchrotron and the irradiation device. Upon input of the timing signal for starting deceleration control from the timing system, the power supply controller may first update the current control data and then select one of the plural deceleration control data items which corresponds to the energy stage reached upon completion of update control so as to make transition to deceleration control.

With this structure, if any one of the component devices making up the charged particle beam irradiation system fails and interrupts ion beam irradiation, direct transition is made to deceleration control so that the operation cycle can be updated safely and in a short time.

Preferably, the interlock system may output the energy change command if the next target energy stage exists upon completion of extraction control at a given energy stage or if the energy stage reached upon completion of initial acceleration control or upon completion of energy change control does not match the next target energy stage. Upon input of the energy change command, the timing system may selectively output the timing signal for energy change control from among the plural control timing signals. Upon input of the timing signal for energy change control, the power supply controller may select one of the plural energy change control data items which corresponds to the given energy stage or to the reached energy stage to perform control so as to make transition to energy change control.

With this structure, if the energy stage is changed without execution of beam extraction, there is no need to perform update control of the extraction control data (involving extraction condition setting control and extraction condition cancellation control). This makes it possible to implement energy change control in a short time and thereby improve the dose rate.

Preferably, the initial acceleration control data item, the plural extraction control data items, the plural energy change control data items, and the plural deceleration control data items may be formed by current/voltage time-series data as controlled variables given directly to the component devices making up the synchrotron.

With this structure, there is no need to calculate parameter changes so that equipment configuration and control device arrangements may be simplified.

Furthermore, in achieving the above and other objects of the present invention, the controller may preferably include: a data storage device for storing a module data as the control data including the initial acceleration control data item, the plural extraction control data items, the plural energy change control data items, and the plural deceleration control data items for permitting beam extraction at all energy stages corresponding to irradiation conditions for a plural predictable patients; and a power supply controller for controlling the component devices making up the synchrotron. Given the irradiation conditions of a specific patent preparatory to irradiation, the controller may select the applicable control data items from among the module data stored in the data storage device and store the selected data items into the power supply controller so as to constitute the operation control data.

With this structure, it is possible to eliminate the wasteful time that does not contribute to beam irradiation (i.e., control time ranging from injection beam energy to irradiation start energy and from irradiation end energy to deceleration end energy on the synchrotron). Beam irradiation over a desired energy range can be performed in a short operation cycle so as to improve the dose rate and shorten treatment time. At the same time, movements of the affected part caused by the patient's physiological activities are detected so that when the position of beam irradiation is found included in the radiation range of the affected part, control may be performed to execute irradiation with the beam.

According to the present invention, during a multistage extraction control operation that implements in a short time the control of changes in the energy of the beam extracted from the synchrotron, beam irradiation over a desired energy range is carried out in a short operation cycle. This improves the dose rate and shortens treatment time.

Also according to the present invention, during the multistage extraction control operation that implements in a short time the control of changes in the energy of the beam extracted from the synchrotron, the operation cycle is updated in a short time if ion beam irradiation is interrupted. This enhances the dose rate and shortens treatment time.

Also according to the present invention, during the multistage extraction control operation that implements in a short time the control of changes in the energy of the beam extracted from the synchrotron, movements of the affected part caused by the patient's physiological activities are detected. When the position of beam irradiation is found included in the radiation range of the affected part, control is performed to execute irradiation. This boosts the dose rate and improves the accuracy of beam irradiation.

DESCRIPTION OF THE PREFERRED EMBODIMENTS

Some preferred embodiments of the present invention are explained below with reference to the accompanying drawings.

Figure 1:
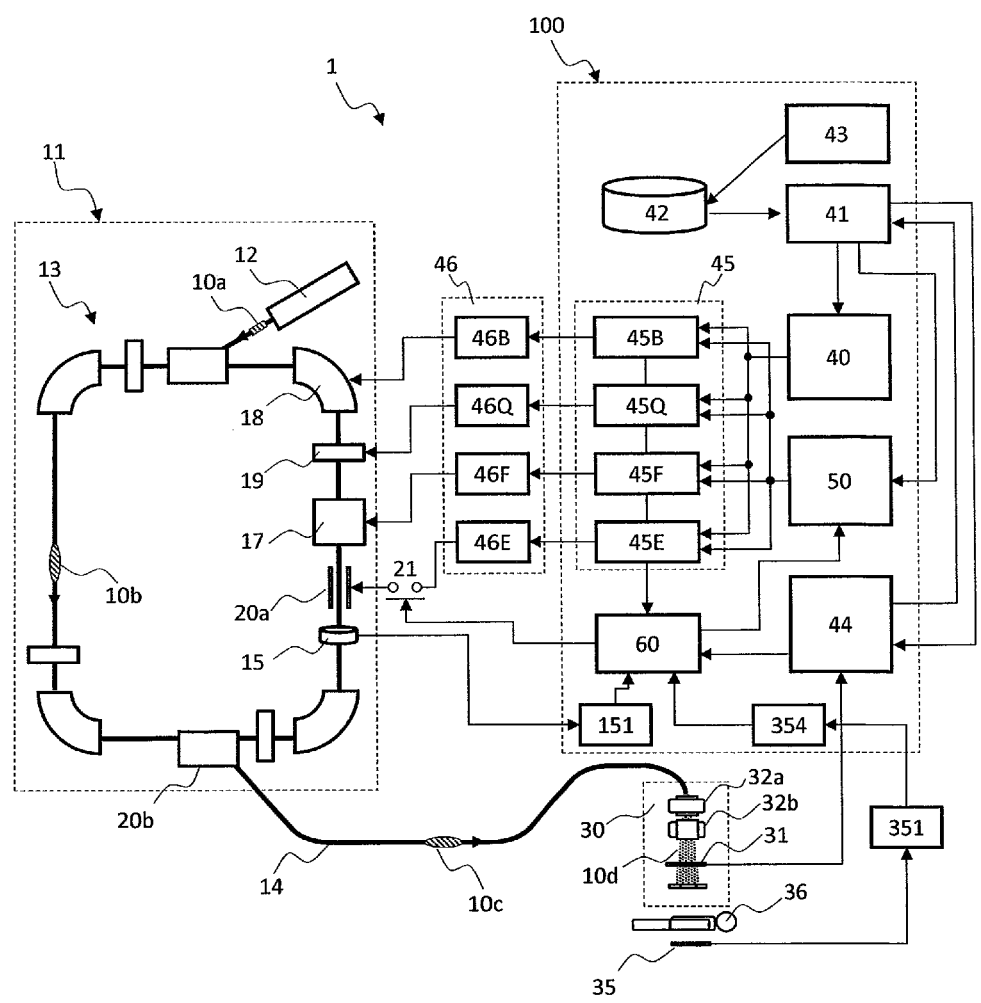
FIG. 1 is a diagram showing a configuration of a charged particle beam irradiation system as one preferred embodiment of the present invention.

FIG. 1 is a diagram showing a configuration of a charged particle beam irradiation system as one preferred embodiment of the present invention.

As shown in FIG. 1, the charged particle beam irradiation system 1 of this embodiment includes an ion beam generator 11, a beam transport device 14, and an irradiation field forming apparatus (charged particle beam irradiation apparatus, simply called the irradiation apparatus hereunder) 30.

The beam transport device 14 connects the ion beam generator 11 with the irradiation apparatus 30 installed inside a treatment room.

The ion beam generator 11 includes an ion source (not shown), a preaccelerator 12, and a synchrotron 13. The ion source is connected to the preaccelerator 12 that in turn is connected to the synchrotron 13. The preaccelerator 12 accelerates an ion beam 10 generated from the ion source up to an energy stage high enough for the beam to be injected into the synchrotron 13. The ion beam 10$a$ accelerated with the preaccelerator 12 is injected into the synchrotron 13.

The synchrotron 13 includes a radio frequency accelerator (accelerating cavity) 17 that applies a radio frequency to the ion beam 10$b$ circulating along a circular path for acceleration up to a target energy stage, a radio frequency extraction electrode 20$a$ that increases a betatron vibration amplitude of the circulating ion beam, and an extraction deflector 20$b$ that takes the ion beam out of its circular path.

The beam 10b injected into the synchrotron 13 is accelerated to a desired energy stage when supplied with the energy of the acceleration radio frequency applied to the radio frequency accelerator 17. At this point, as the circulating energy of the ion beam 10b is being raised, the magnetic field intensities of a bending magnet 18 and a quadrupole magnet 19 together with the frequency of the radio frequency voltage applied to the accelerating cavity 17 are increased correspondingly so that the circular path of the ion beam 10b circulating inside the synchrotron 13 remains constant.

After the ion beam 10b has been accelerated to the desired energy stage, control is performed to set extraction conditions so as to regulate the excitation amounts of the quadrupole magnet 19 and of a hexapole magnet (not shown) in a manner establishing the conditions under which the circulating ion beam 10b can be extracted (i.e., stability limit conditions for the circulating beam).

Upon completion of extraction condition setting control, an extraction radio frequency voltage is applied to the radio frequency extraction electrode 20a in order to increase the betatron vibration amplitude of the beam 10b circulating inside the synchrotron 13. The increase in the betatron vibration amplitude causes the circulating beam 10b having exceeded the stability limit conditions to be extracted from the synchrotron 13 toward the beam transport device 14. The beam transport device 14 transports the extracted beam to the irradiation apparatus 30. Control of beam extraction from the synchrotron 13 can be implemented at high speed with a radio frequency switch 21 performing control to turn on and off the radio frequency voltage applied to the radio frequency extraction electrode 20a.

Upon completion of the control of beam extraction from the synchrotron 13, control is performed to cancel the extraction conditions so as to regulate the excitation amounts of the quadrupole magnet 19 and hexapole magnet (not shown) in a manner canceling the stability limit conditions established for the circulating beam 10b at the time of setting the extraction conditions.

Upon completion of extraction condition cancellation control, the ion beam 10b circulating inside the synchrotron 13 is decelerated by lowering the magnetic field intensities of the bending magnet 18 and quadrupole magnet 19 together with the frequency of the radio frequency voltage applied to the accelerating cavity 17. Transition to the next operation cycle is thus performed.

The irradiation apparatus 30 controls an ion beam 10c guided by the beam transport device 14 so as to irradiate an affected part 37 of a patient 36 on the treatment couch in conformity with the shape of the affected part 37 and its depth from the patient's body surface. The irradiation apparatus 30 operates by the scanning irradiation method. Because the scanning irradiation method allows the affected part 37 to be irradiated directly with an ion beam 10d, the efficiency of ion beam utilization is high. This method further permits irradiation of the affected part with the ion beam 10d in a manner more conforming to the affected part shape than the existing scattering irradiation method.

The irradiation range in the depth direction of the affected part is adjusted by changing the energy stage of the ion beam, whereby the desired affected part is irradiated. Particularly with the scanning irradiation method, the ion beam 10b circulating inside the synchrotron 13 is adjusted in energy before being extracted so as to adjust the irradiation range of the ion beam to the depth of the affected part 37. This requires changing the energy stage a number of times during radiation treatment of the patient.

The methods for irradiating the affected part with the beam in the planar direction include a spot scanning irradiation method and a raster scanning irradiation method.

According to the spot scanning irradiation method, the irradiation plane of the affected part is divided into dose-managed regions called spots; scanning is stopped at each spot to irradiate it with the beam until a predetermined dose is reached; the beam is then stopped at that point, and the next spot is reached for irradiation. In this manner, the spot scanning irradiation method involves updating the irradiation starting position at each spot.

According to the raster scanning irradiation method, the dose-managed regions are set as with the spot scanning irradiation method. However, beam scanning is not stopped on a spot-by-spot basis. Instead, the scanning path is scanned with the beam for irradiation. For this reason, the uniformity of irradiation doses is improved by execution of repainting irradiation whereby irradiation is repeated at a reduced dose per round of irradiation. Thus the raster scanning irradiation method involves updating the irradiation starting position per scanning path.

Under control by the spot scanning method, as with the raster scanning method, the dose per round of irradiation at each spot may be set low and the irradiation plane may be scanned a number of times until an ultimate target dose is reached.

Figure 2:
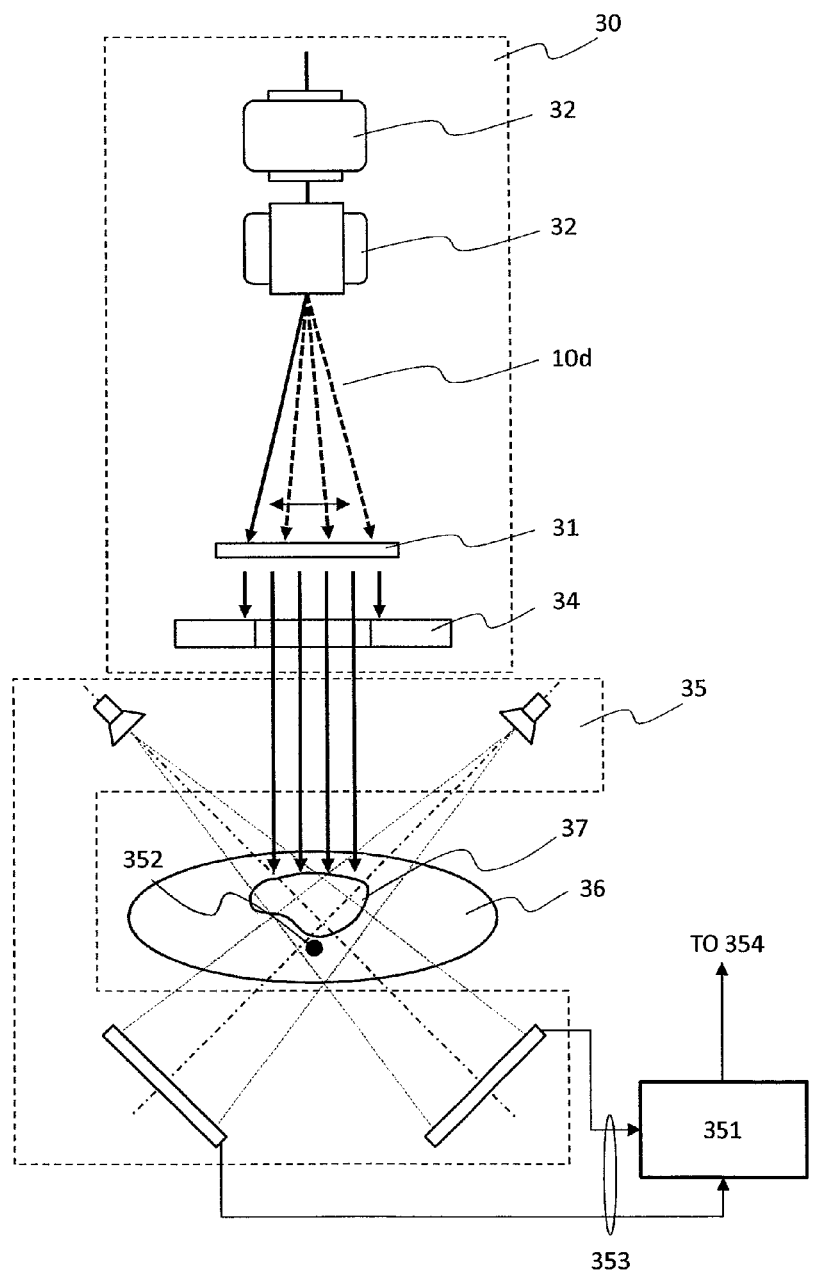
FIG. 2 is a diagram showing a structure of an irradiation device operating by a scanning irradiation method as one embodiment of the present invention.

FIG. 2 shows a structure of the irradiation apparatus 30. The irradiation apparatus 30 has scanning magnets 32a and 32b. The scanning magnets 32a and 32b allow the affected part plane to be scanned with the beam in conformity with the shape of the affected part. The irradiation apparatus 30 also has a dose monitor 31 that measures the dose of the beam 10d with which the patient is irradiated, and a beam shape monitor (not shown). These devices are used successively to monitor the dose and the shape of the irradiation beam 10d. The beam 10d subjected to the scanning magnets 32 for scanning forms an irradiation field through a collimator 34 in conformity with the affected part 37 of the patient 36.

If the affected part is a respiratory moving organ, control is required so that the movement of the affected part 37 be detected and the affected part 37 be irradiated with the beam only when the affected part 37 is in a predetermined position in order to achieve highly accurate irradiation of the affected part 37 with the beam.

Thus as shown in FIG. 2, there are provided an affected part position detection unit 35 and an extraction permission determination unit 354. A marker 352 is provided near the affected part 37 so as to identify the position of the part. The marker 352 is detected with a transparent image acquisition unit 351. Transparent image information acquired with the transparent image acquisition unit 351 is input to the extraction permission determination unit 354. It is then determined whether the position of the marker 352 indicated by the transparent image information is included in a beam irradiation permission range 353. If it is determined that the position of the marker 352 indicated by the transparent image information is included in the beam irradiation permission range 353, the extraction permission determination unit 354 outputs to an interlock system 60 an extraction permission determination signal 355 permitting beam extraction. If it is determined that the position of the marker 352 indicated by the transparent image information is not included in the beam irradiation permission range 353, beam extraction is not permitted. Thus the extraction permission determination unit 354 does not output the extraction permission determination signal 355.

Where the affected part position detection unit 35 and extraction permission determination unit 354 are provided to control beam extraction from the synchrotron 13 on the basis of the extraction permission determination signal 355, it is possible to perform control so that the affected part 37 is irradiated with the beam only when the affected part 37 is in a predetermined position.

Returning to FIG. 1, the charged particle beam irradiation system 1 of this embodiment is equipped with a control system 100 (controller).

The control system 100 includes an accelerator controller 40, a main controller 41, a treatment planning device 43, a data storage device 42, an irradiation controller 44, a timing system 50, the interlock system 60, a power supply controller 45, a remaining beam amount measurement unit 151, and the extraction permission determination unit 354.

The accelerator controller 40 controls the ion beam generator 11 and beam transport device 14. The main controller 41 integrally controls the charged particle beam irradiation system 1 as a whole. The treatment planning device 43 plans beam irradiation conditions for the patient. The data storage device 42 stores the information planned by the treatment planning device 43 as well as control information regarding the synchrotron 13 generating the ion beam and the beam transport device 14. The irradiation controller 44 controls the component devices making up the irradiation apparatus 30 and the dose of the ion beam 10*d* with which the affected part 37 is irradiated. Also, the irradiation controller 44 calculates a cumulative dose of each dose-managed region from dose measurement data 311 measured successively with the dose monitor 31, and acquires a residual dose from the cumulative dose and from the target dose with which the affected part is irradiated. The timing system 50 provides synchronizing control over the component devices making up the synchrotron 13. The interlock system 60 is independent of the main controller 41 so as to guarantee the safety of the patient 36. The power supply controller 45 controls a power supply 46 for the component devices making up the synchrotron 13. The remaining beam amount measurement unit 151 prepares data about the amount of the beam accumulated in the synchrotron 13 (remaining beam amount measurements 152) as measured by use of a remaining beam amount monitoring unit 15.

The data storage unit 42 may be provided as part of the main controller 41.

The power supply 46 is a collective term representing the power supplies for the plural devices making up the synchrotron 13. Shown in FIG. 1 as the power supplies of the plural devices are a power supply 46B of the bending magnet 18, a power supply 46Q of the quadrupole magnet 19, a power supply 46F of the radio frequency accelerating cavity 17, and a power supply 46E of the radio frequency extraction electrode 20*a*.

As with the power supply 46, the power supply controller 45 is a collective term representing plural power supply controllers corresponding to the plural power supplies of the component devices. Shown in FIG. 1 are a controller 45B of the power supply 46B, a controller 45Q of the power supply 46Q, a controller 45F of the power supply 46F, and a controller 45E of the power supply 46E.

Explained below are some of the items studied by the inventors with reference to the above-cited literature.

Figure 9:
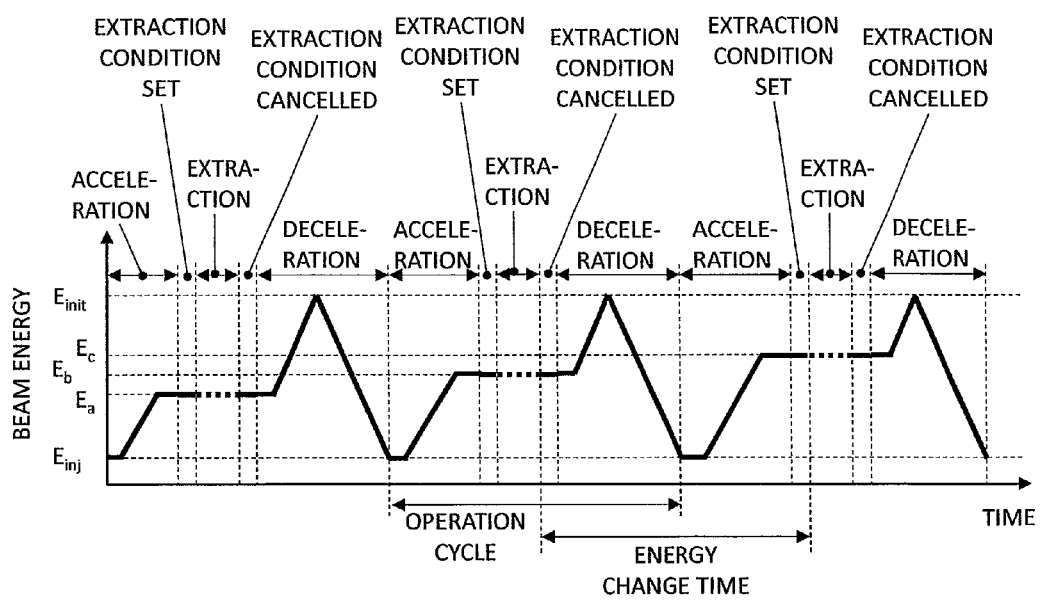
FIG. 9 is a diagram showing an operation sequence of an ordinary synchrotron.

FIG. 9 shows an operation sequence of the ordinary synchrotron 13. The synchrotron 13 performs a series of controls including acceleration, extraction, and deceleration in one operation cycle. Before and after extraction control, specific controls are needed. Before extraction control, control is required to set the extraction conditions necessary for extracting the ion beam from the synchrotron; after extraction control, control is required to cancel the extraction conditions.

Where the ordinary synchrotron 13 is controlled in operation, control data corresponding to the series of controls are stored as pattern data in a memory of the power supply controller 45. The power supply controller 45 updates the control data on the basis of a timing signal 51 output from the timing system 50 that manages the control timings of the component devices making up the synchrotron 13.

As shown in FIG. 9, the synchrotron 13 performs controls ranging from acceleration to deceleration in one operation cycle. For this reason, to change the energy stage of the ion beam 10*c* to be extracted requires updating the operation cycle after the remaining beam is decelerated by making transition to deceleration control upon completion of extraction control. After the operation cycle is updated, the ion beam 10*b* is again accelerated to implement control for changing to the desired energy stage.

As a result, where the ordinary synchrotron 13 is controlled in operation, it takes almost as much time to change the energy stage of the ion beam 10*b* as one operation cycle. This prolongs treatment time and poses a problem in improving the dose rate.

Japanese Patent No. 4873563 discloses the multistage extraction control operation of the ion synchrotron whereby the ion beam is extracted at the plural energy stages within one operation cycle. This type of multistage extraction control operation helps shorten the time required to change the energy stage by the scanning irradiation method.

Non-patent Document 1 describes how stepped operation control data formed by energy change and extraction controls and corresponding to the plural energy stages extracted from the ion synchrotron are prepared beforehand (page 34, FIG. 2), and how operations are carried out (page 35, FIG. 3) to extend the flat portion of the operation control data regarding an extraction control unit and corresponding to the energy stage of the ion beam to be extracted.

As explained in Non-patent Document 1, if control is performed whereby the operation control data permitting extraction at the plural energy stages are prepared beforehand as the pattern data and if the ion beam necessary for completing all irradiation has been accumulated in the synchrotron, the described arrangement provides the effect of completing irradiation at all energy stages in one operation cycle. However, if the ion beam necessary for completing all irradiation has not been accumulated in the synchrotron, it is necessary to perform deceleration control when the ion beam is exhausted, before updating the operation cycle to again inject and accelerate the ion beam 10*b*. At this point, to make transition from energy extraction control with the exhausted ion beam to deceleration control requires taking into account the continuity of the operation control data. That in turn requires updating all operation control data for energy change control stored subsequent to the energy stage at which the ion beam 10*b* was exhausted. Direct transition cannot be made from extraction control using the operation control data in question to deceleration control. For this reason, it takes an inordinate time to update the operation cycle of the synchrotron 13. Also, in the event of a failure in any one of the component devices making up the charged particle beam irradiation system 1, the problem remains that direct transition cannot be made from extraction control using the operation control data to deceleration control.

JP-2011-124149-A describes the magnetic field reference generation unit that outputs magnetic flux density information corresponding to elapsed time with reference to the coil current which excites the magnetic field coil of the accelerator, and the current reference conversion unit that obtains the coil current which generates the magnetic field corresponding to the magnetic flux density information. The magnetic flux density information from the magnetic field reference generation unit is output in a combination of four patterns (initial rise pattern, decrease pattern, increase pattern, and completion pattern) by a control method that implements beam extraction at the plural energy stages within one operation cycle.

According to JP-2011-124149-A, ion beam extraction is made available at the plural energy stages in one operation cycle by suitably combining the four magnetic flux density patterns. Meanwhile, the timing signals that command the combination sequences of the four patterns by selecting the operation control data on the synchrotron are written beforehand in the timing controller. As a result, direct transition from extraction control at the extraction energy to deceleration control cannot be made so as to guarantee the continuity of set values. Because rapid deceleration control is not available when the beam is exhausted or in the event of a device failure, it takes time to update the operation cycle of the synchrotron. Since a current reference converter is used successively to calculate and output the exciting currents of the bending magnet and quadrupole magnet, operation parameters need to be changed every time the pattern is changed. This poses the problem of complicating the equipment configuration and control arrangements.

Japanese Patent No. 2921433 and JP-2013-111406-A describe the control method whereby the beam is extracted from the synchrotron 13 on the basis of the detected movements of the affected part 37 caused by its physiological activities so that the affected part 37 may be accurately irradiated with the beam even when the affected part 37 is a respiratory moving organ.

According to Japanese Patent No. 2921433, if a movement of the affected part 37 is detected upon control of beam extraction from the synchrotron 13, beam extraction control is stopped and then transition is made to deceleration control. Subsequently, the beam acceleration and extraction conditions necessary for the next stage of irradiation are established. If transition is made to deceleration control the moment the output of the extraction permission control signal is stopped, then deceleration takes place while there still remains the beam circulating inside the synchrotron. This poses the problem of not being able to implement the multistage extraction control operation involving changing the energy of the circulating beam in the operation cycle as aimed at the present invention.

According to JP-2013-111406-A, transition is not made to deceleration control as soon as the output of the extraction permission control signal is stopped. Instead, transition is made to a standby state over a predetermined time period. If the extraction permission signal is again input in the standby state, beam extraction is resumed. This can make the efficiency of beam utilization higher than with Japanese Patent No. 2921433. In this case, however, transition is made to deceleration control upon elapse of the waiting time, so that it is impossible to implement the multistage extraction control operation involving changing the energy of the circulating beam in the operation cycle as in the case of Japanese Patent No. 2921433. The problem thus remains that the efficiency of utilization of the beam circulating inside the synchrotron is low.

The present invention aims a multistage extraction control operation that permits extraction of an ion beam at the plural energy stages within one operation cycle of the synchrotron. This invention is intended to provide an ion synchrotron capable of implementing beam energy change control and operation cycle update, as well as highly accurate beam irradiation even where the affected part 37 is a respiratory moving organ. The operation is explained below in detail.

Explained first with reference to FIGS. 3 through 8 are the structure of control data in effect in the multistage extraction operation characteristic of this embodiment, and the operation sequence that uses the control data.

Figure 3:
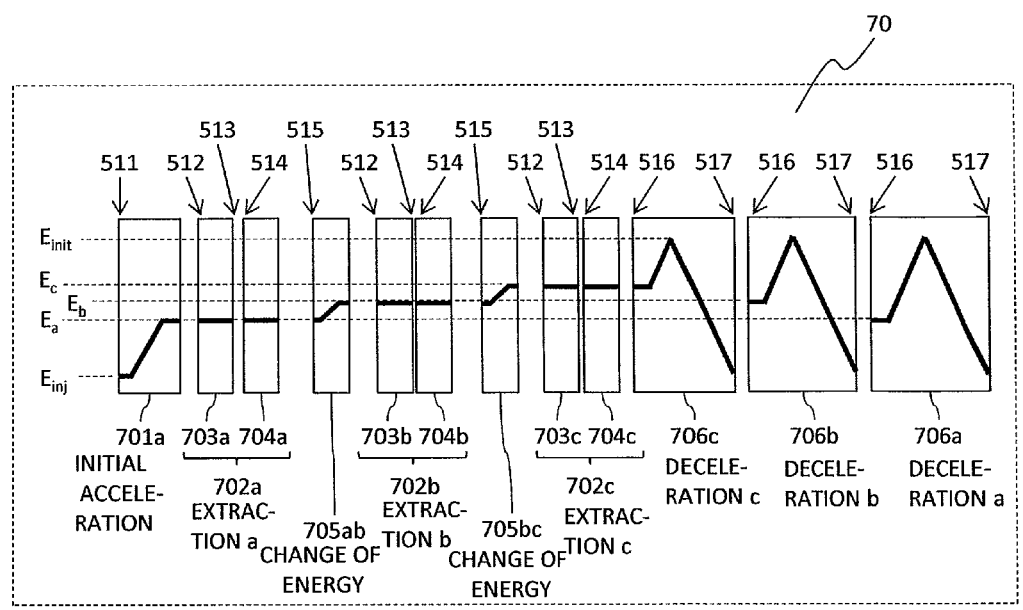
FIG. 3 is a diagram showing a structure of control data about a plural devices making up a synchrotron as one embodiment of the present invention.

FIG. 3 is a diagram showing a structure of control data about the plural devices making up the synchrotron. As a representative example of the device control data, the exciting current for the bending magnet 18 is shown. With this embodiment, three stages of data are shown for purpose of explanation. In practice, as described in Non-patent Document 1, there are provided as many stages of data as the number of the energy stages of the beam for irradiation. Whereas this embodiment is shown to use the operation control data whereby irradiation with the beam is performed at energy stages ranging progressively from low to high, the same effects are obtained when beam irradiation is carried out at energy stages ranging successively from high to low.

Figure 4:
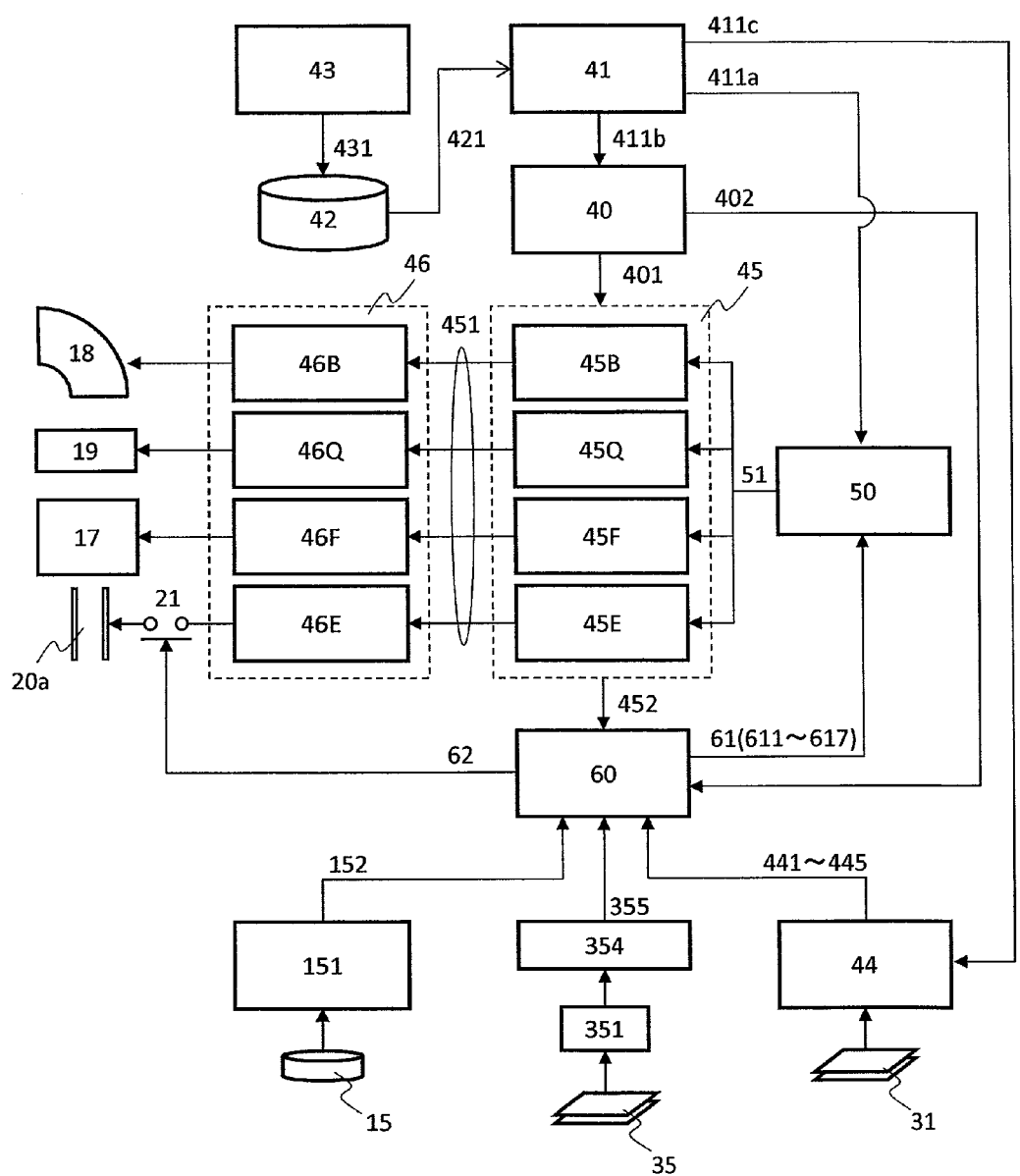
FIG. 4 is a diagram showing a configuration of a control system (controller) for implementing a multistage extraction operation as one embodiment of the present invention, the diagram also depicting how information is transferred between the devices making up the control system.
Figure 5:
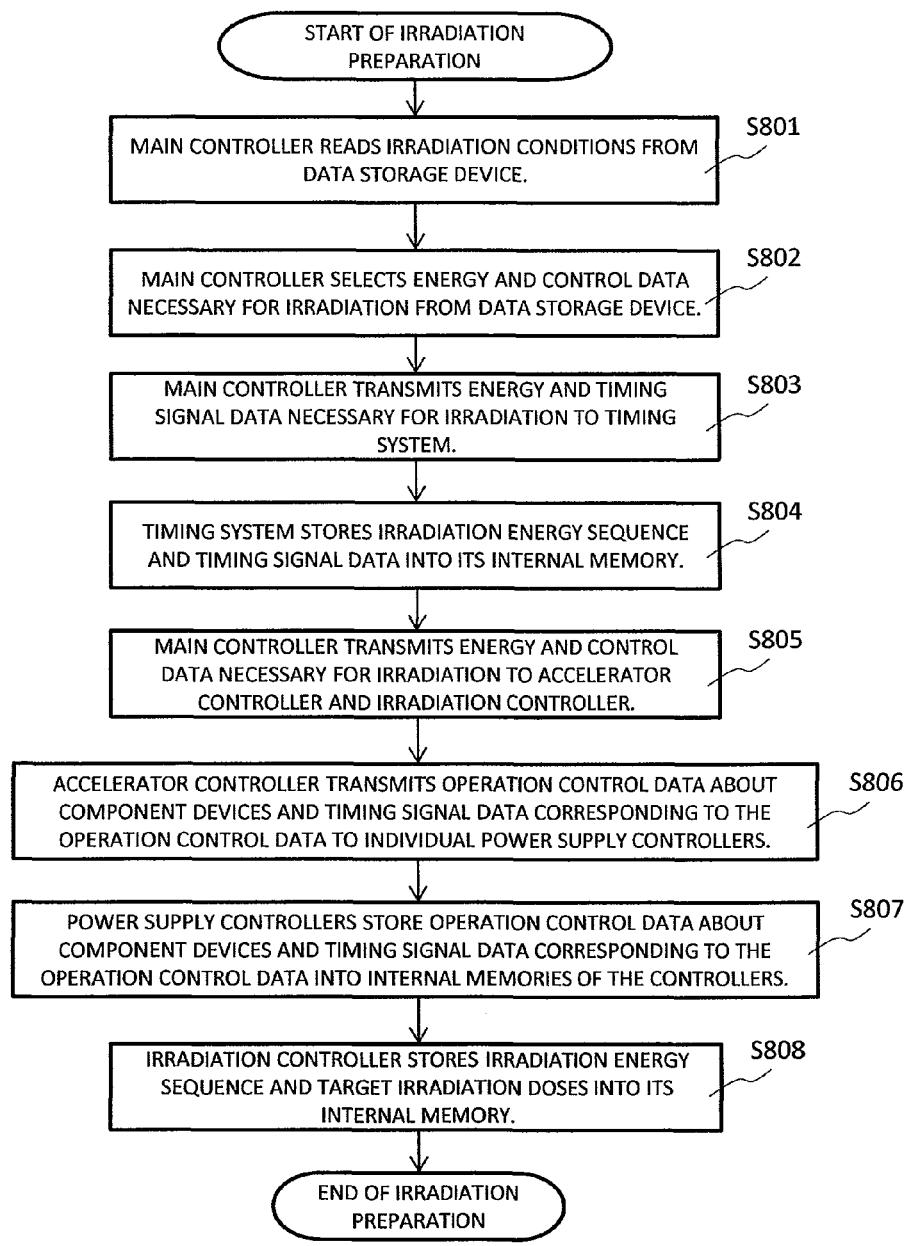
FIG. 5 is a flowchart showing an irradiation preparation flow in effect before the start of the multistage extraction operation as one embodiment of the present invention.
Figure 6:
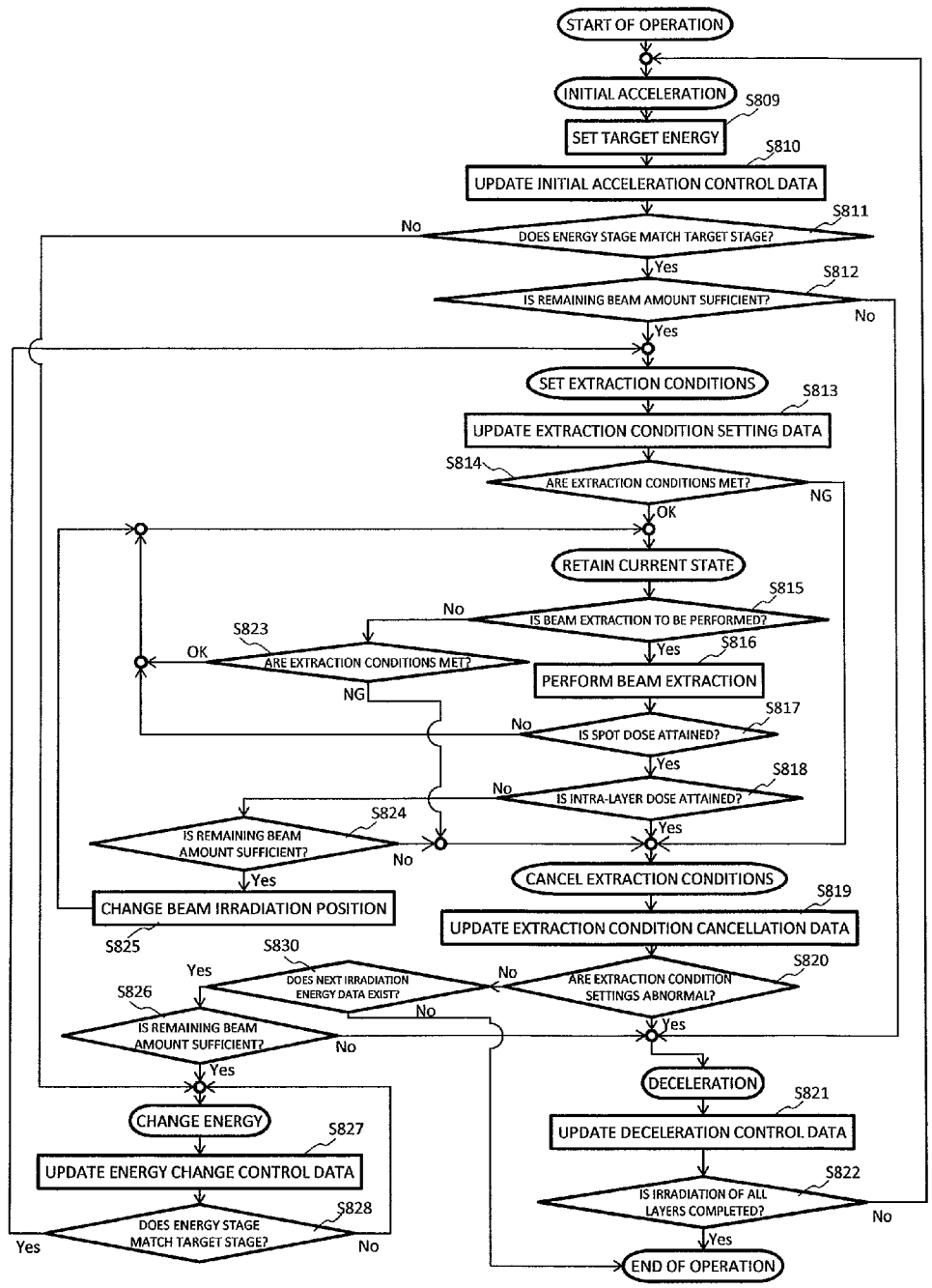
FIG. 6 is a flowchart showing a control flow (state transitions) in effect during the multistage extraction operation as one embodiment of the present invention.
Figure 7A:
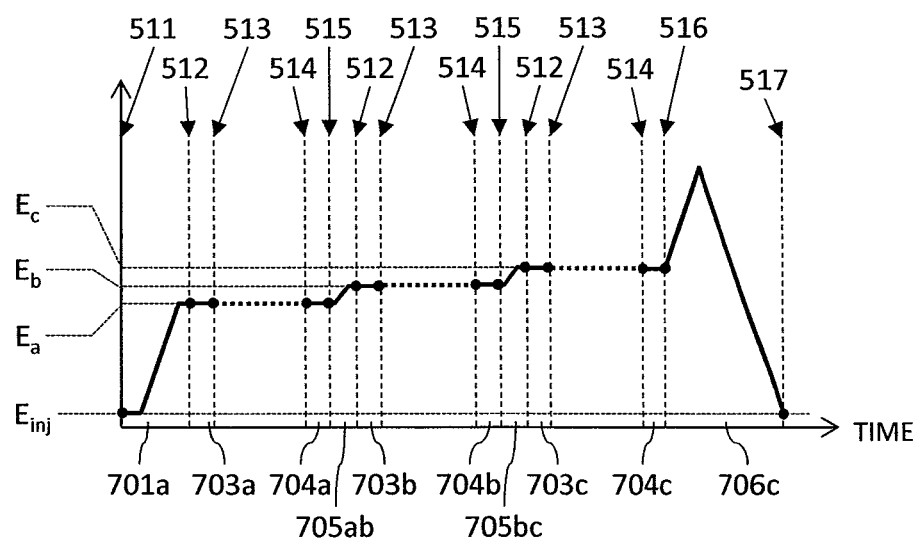
FIG. 7A is a diagram showing an example of the control data being output during the multistage extraction operation involving a combination of the control data items indicated in FIG. 3, as one embodiment of the present invention.
Figure 7B:
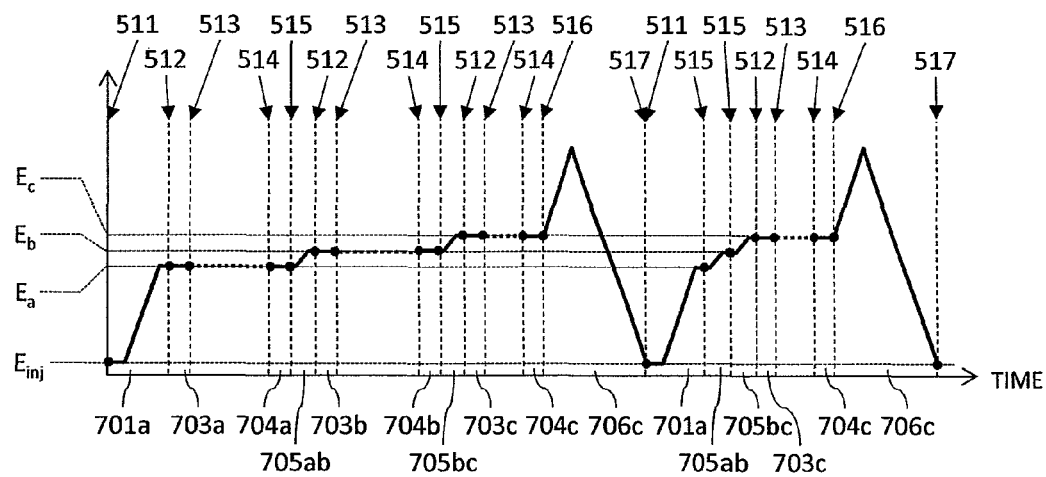
FIG. 7B is a diagram showing another example of the control data being output during the multistage extraction operation involving a combination of the control data items indicated in FIG. 3, as one embodiment of the present invention.
Figure 8:
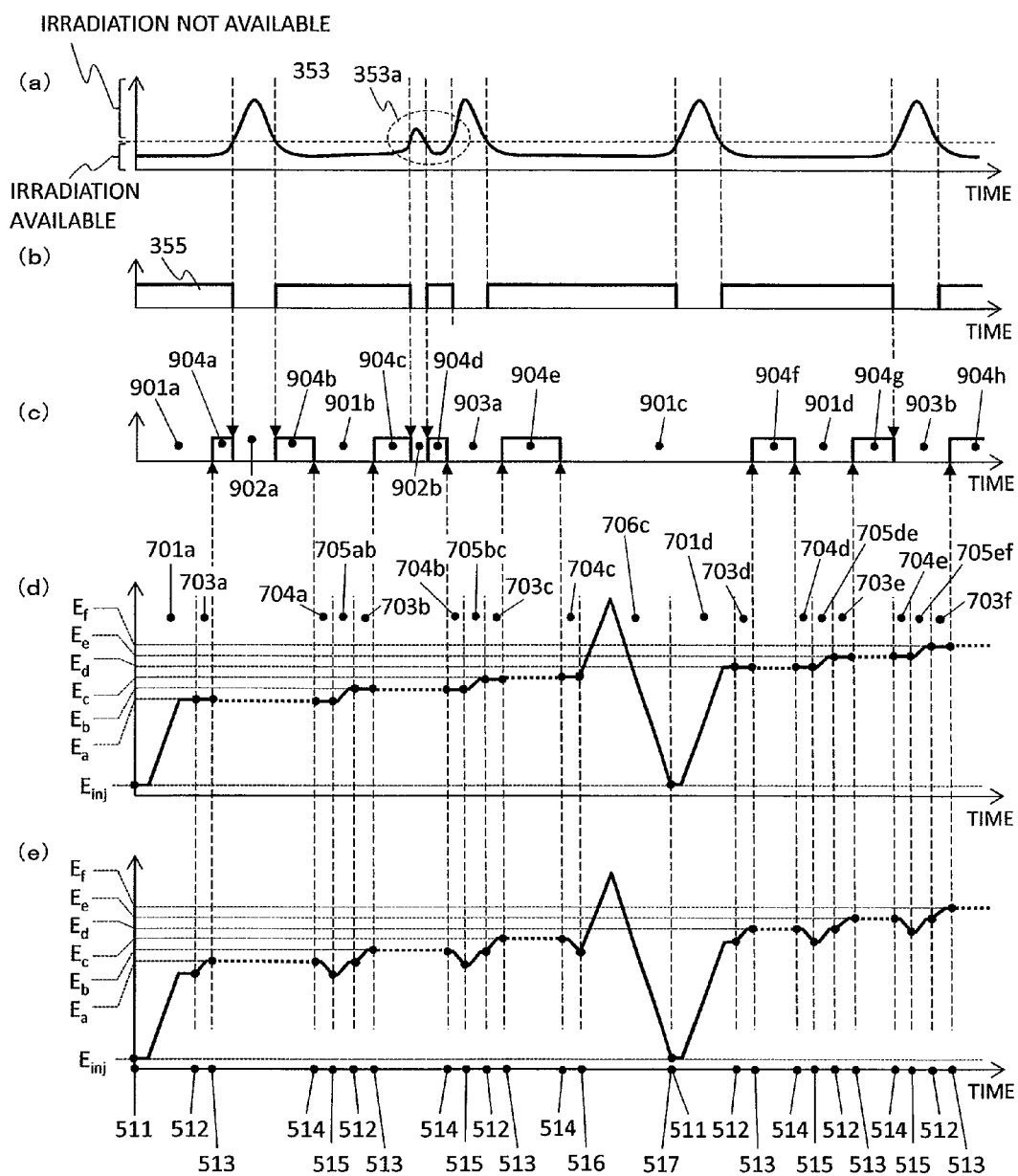
FIG. 8 is a set of diagrams showing an example of the control data being output for irradiation of a respiratory moving organ during the multistage extraction operation involving a combination of the control data items indicated in FIG. 3, as one embodiment of the present invention.

FIG. 4 is a diagram showing a configuration of the control system (controller) 100 for implementing the multistage extraction operation characteristic of this embodiment, the diagram also depicting how information is transferred between the devices making up the control system. FIG. 5 is a flowchart showing an irradiation preparation flow in effect before the start of the multistage extraction operation. FIG. 6 is a flowchart showing a control flow (state transitions) in effect during the multistage extraction operation. FIGS. 7A and 7B are diagrams showing examples of the control data being output during the multistage extraction operation involving combinations of the control data items indicated in FIG. 3. FIG. 8 is a set of diagrams showing an example of the control data being output for irradiation of a respiratory moving organ during the multistage extraction operation.

As shown in FIG. 3, the operation control data 70 regarding the devices (bending magnet 18 in the illustrated example) making up the synchrotron are made up of an initial acceleration control data item 701a (represented by 701 hereunder), a plural extraction control data items 702a through 702c (represented by 702 hereunder) for ion beam extraction at the plural energy stages (three energy stages Ea, Eb and Ec in this example), a plural energy change control data items 705ab and 705bc (represented by 705 hereunder) connecting the plural extraction control data items 702, and a plural deceleration control data items 706a through 706c (represented by 706 hereunder) corresponding to the plural extraction control data items 702.

The plural extraction control data items 702 are formed by a plural extraction condition setting data items 703a through 703c (represented by 703 hereunder) for setting the operation conditions necessary for beam extraction from the synchrotron 13, and by a plural extraction condition cancellation data items 704a through 704c (represented by 704 hereunder) for canceling the extraction conditions so as to make transition to the changing of circulating beam energy or to deceleration control after the stop of beam extraction from the synchrotron 13.

The plural deceleration control data items 706 include initial values that correspond to the extraction energy stages of the plural extraction control data items 702, and final values that correspond to injection energy stages of the synchrotron 13. This data structure permits direct transition from extraction control at the extraction energy to deceleration control if the irradiation with the ion beam is interrupted.

Extraction of the beam at the plural energy stages is controlled by suitably combining the control data items 701, 702 and 705. Because there are provided the plural deceleration control data items 706 corresponding to the plural extraction energy stages, rapid transition can be made from any extraction energy stage to deceleration control.

These control data items 701, 702, 705 and 706 are provided as current/voltage time-series data constituting controlled variables that are fed directly to the devices involved.

For example, the control data items regarding the bending magnet 18 are made up of the time-series data of exciting currents and voltages (not shown) to be set to the bending magnet power supply 46B and needed for generating predetermined bending magnetic field intensities.

These control data items 701, 702, 705 and 706 are stored in the data storage device 42. The data storage device 42 stores as module data the control data items for permitting beam extraction at all energy stages corresponding to the irradiation conditions for all predictable patients as well as the control data items shown in FIG. 3.

For example, if the number of energy stages for extraction corresponding to a plural predictable patients is 100, the data storage device 42 stores, as the module data items, 100 initial acceleration control data items 701, 100 extraction control data items 702, 99 energy change control data items 705, and 100 deceleration control data items 706. Given the irradiation conditions of a specific patent preparatory to irradiation, the main controller 41 selects the applicable control data items from among those stored in the data storage device 42 and stores the selected data items into the power supply controller 45.

The module data items for permitting beam extraction at all energy stages may be stored in an internal storage device of the main controller 41.

The operation control data items 70 are related individually to the timing signals 51 output from the timing system 50.

The timing signals 51 of this embodiment are made up of an acceleration control start timing signal 511, an extraction condition setting timing signal 512, an extraction control wait timing signal 513, an extraction condition cancellation timing signal 514, an energy change control timing signal 515, a deceleration control start timing signal 516, and a deceleration control end timing signal 517.

When the timing signal 51 is input to the power supply controller 45, the power supply controller 45 selects the control data related to the input timing signal 51 and starts updating from the initial address of the selected control data.

Explained below with reference to FIG. 3 is how update control of the operation control data 70 is performed in response to the input timing signal 51.

When the acceleration control start timing signal 511 is input, the power supply controller 45 updates the initial acceleration control data 701a ranging from an injection energy stage (Einj) to an initial extraction energy stage (Ea) in order to accelerate the beam.

When the extraction condition setting timing signal 512 is input, the plural extraction condition setting data items 703a are updated.

Upon beam extraction control, stable beam extraction is performed by controlling to constant values the excitation amounts of the bending magnet 18, quadrupole magnet 19, and hexapole magnet (not shown), as well as the radio frequency voltage applied to the radio frequency accelerating cavity 17. This involves stopping the update of the plural extraction condition setting data items 703a upon input of the extraction control wait timing signal 513 and waiting for the extraction condition cancellation timing signal 514 to be input. The beam is extracted from the synchrotron 13 when the radio frequency switch 21 is closed upon input of the extraction permission determination signal 355 so as to supply the radio frequency voltage to the radio frequency extraction electrode 20a for extraction purposes.

When transition is to be made to deceleration or energy change control upon completion of beam extraction control, the update of the plural extraction condition cancellation data items 704a is started upon input of the extraction condition cancellation timing signal 514 in order to cancel the extraction conditions.

Before the end of the update of the plural extraction condition cancellation data items 704a, the interlock system 60 chooses to output either the energy change timing signal 515 or the deceleration control start timing signal 516 on the basis of the detected remaining beam amount measurements 152 inside the synchrotron 13 and the remaining dose given as the difference between the target dose and the current dose at the current energy stage. As a result of the selection by the interlock system 60, a command is issued to output either the energy change control timing signal 515 or the deceleration control start timing signal 516 to the timing system 50.

The control data items making up the operation control data 70 are arranged so that the exit value of the plural extraction condition cancellation data items 704 is the same as the starting value of the plural energy change control data items 705 for transition to the next irradiation energy stage (e.g., the exit value of 704a being equal to the starting value of 705ab in FIG. 3) and that the exit value of the plural extraction condition cancellation data items 704 is the same as the starting value of the plural deceleration control data items for deceleration down to the injection energy stage (e.g., the exit value of 704a being equal to the starting value of 706a in FIG. 3), whereby the continuity between the control data items is ensured.

When operation control is thus implemented on the basis of the input timing signals 51, it is easy to provide the changing and updating of the operation control data items 70 in accordance with the timing signals 51.

When the multistage extraction operation above is carried out, the interlock system 60 outputs interlock control commands 61 on the basis of beam energy information 402 output from the accelerator controller 40; an energy change request signal 443, a deceleration control request signal 444, and an irradiation completion signal 445 output from the irradiation controller 44; status information 452 output from the power supply controller 45 indicative of device integrity; the remaining beam amount measurement data 152 from the remaining beam amount monitoring unit 15, and the extraction permission determination signal 355 from the affected part position detection unit 35.

The interlock control commands 61 include an initial acceleration command 611, an irradiation preparation command 612, an irradiation wait command 613, an irradiation stop command 614, an energy change command 615, a deceleration control command 616, and an irradiation complete command 617.

The timing system 50 outputs the energy change control timing signal 515 on the basis of the energy change command 615 output from the interlock system 60. Also, the timing system 50 outputs the extraction condition setting timing signal 512 on the basis of the irradiation preparation command 612 from the interlock system 60. The timing system 50 further outputs the extraction condition cancellation timing signal 514 on the basis of the irradiation stop command 614 from the interlock system 60. The timing system 50 also outputs the deceleration control start timing signal 516 on the basis of the deceleration control command 616. The timing system 50 further outputs a beam extraction command 62 to the radio frequency switch 21 on the basis of the extraction permission determination signal 355 from the extraction permission determination unit 354 so as to control the supply of the radio frequency voltage to the radio frequency extraction electrode 20a for extraction purposes.

Explained below with reference to FIGS. 4 and 5 is the irradiation preparation flow in effect when the multistage extraction operation is performed by use of the control data shown in FIG. 3 regarding the component devices making up the synchrotron.

First, the treatment planning device 43 registers treatment plan information 431 including the irradiation conditions necessary for treating the patient in the data storage device 42. On the basis of the setting information about the irradiation conditions, the main controller 41 reads the irradiation conditions 421 from the data storage device 42 (step S801).

Given the irradiation conditions, the main controller 41 selects from the data storage device 42 the energy stages and doses necessary for irradiation, the irradiation sequence involved, and the control data (step S802). As mentioned above, the data storage device 42 stores as the module data the control data items for permitting irradiation with the beam at all energy stages corresponding to the irradiation conditions of all predictable patients, the control data items including the initial acceleration control data item 701, the plural extraction control data items 702, the plural extraction condition setting data items 703, the plural extraction condition cancellation data items 704, the plural energy change control data items 705, and the plural deceleration control data items 706 shown in FIG. 3. The main controller 41 selectively reads the control data items 701 through 706 on the basis of the irradiation conditions 421.

The main controller 41 then transmits to the timing system 50 the energy stage information necessary for irradiation, the irradiation sequence, and timing signal data 411a corresponding to the energy stages involved (step S803).

In turn, the timing system 50 stores into its memory the energy stage information necessary for irradiation, the irradiation sequence, and the timing signal data 411a corresponding to the energy stages involved, all transmitted from the main controller 41 (step S804). Similarly, the main controller 41 transmits the energy stage information necessary for irradiation, the irradiation sequence, and control data items 411b and 411c corresponding to the energy stages involved to the accelerator controller 40 and irradiation controller 44 (step S805). The control data items 411b transmitted to the accelerator controller 40 include the operation control data items about the devices involved (control data items 701 through 706) and the timing signals corresponding to the operation control data items (timing signals 511 through 517). The control data items 411c transmitted to the irradiation controller 44 include the sequence of irradiation at the energy stages involved and the target doses.

The accelerator controller 40 then transmits data items 401 formed by the operation control data items about the devices involved (control data items 701 through 706) and by the timing signals corresponding to the operation control data items (timing signals 511 through 517) to the individual power supply controllers 45 of the component devices making up the synchrotron 13 and beam transport device 14 (step S806). The power supply controllers 45 store into their internal memories the data items 401 made up of the operation control data items about the devices and of the timing signals corresponding to the operation control data items (step S807).

Thereafter, the irradiation controller 44 stores into its memory the sequence of irradiation at the energy stages involved and the target doses (step S808).

Explained below with reference to FIGS. 4 and 6 is the irradiation flow in effect when the multistage extraction operation is carried out by use of the control data items shown in FIG. 3 regarding the component devices making up the synchrotron.

When the user inputs an irradiation start command (not shown) to the main controller 41, the operation control of the synchrotron 13 is started.

The main controller 41 first outputs a control start command 412 designating the start of an operation cycle of the synchrotron 13 to the timing system 50, accelerator controller 40, and irradiation controller 44. The timing system 50, accelerator controller 40, and irradiation controller 44 set a target energy stage on the basis of the control start command 412 (step S809).

After verifying that the devices are operating normally, the interlock system 60 outputs the initial acceleration command 611 on the basis of the set target energy stage. The timing system 50 sets target energy stage information on the beam about to be extracted, and the accelerator controller 40 sets the target energy stage for the individual power supply controllers. Given the target energy stage, the irradiation controller 44 sets the target doses for the dose-managed regions involved regarding the energy stage of interest.

Although not shown in FIG. 6, if any power supply controller 45 detects an anomaly in the status information 452 about the corresponding power supply 46, the interlock system 60 has the capability to stop beam irradiation and let the synchrotron 13 transition to deceleration control.

On the basis of the control start command 412, the timing system 50 then outputs the acceleration control start timing signal 511. The power supply controllers 45 start updating the initial acceleration control data item 701 (step S810).

Later, upon completion of initial acceleration control, the accelerator controller 40 outputs the beam energy information 402 to the interlock system 60. On the basis of the beam energy information 402 sent from the accelerator controller 40, the interlock system 60 determines whether the energy stage reached at the end of acceleration matches the target energy stage (step S811).

If it is determined in step S811 that the target energy stage does not match the energy stage reached upon completion of initial acceleration control, it may be the case where, during the multistage extraction control operation, the execution of energy change control (to be discussed later) subsequent to the initial acceleration energy stage is followed by the execution of deceleration control as a result of the remaining beam being exhausted or a device having failed, so that beam irradiation is performed again at the energy stage in effect following energy change control. Where the energy stage reached upon completion of acceleration does not match the target energy stage, the interlock system 60 outputs the energy change command 615 to the timing system 50. The timing system 50 outputs the energy change control timing signal 515 to the power supply controllers 45. In turn, the power supply controllers 45 update the plural energy change control data items 705 (step S827).

If it is determined in step S811 that the energy stage reached at the end of acceleration matches the target energy stage, the interlock system 60 verifies the remaining beam amount measurements 152 from the remaining beam amount monitoring unit 15 to determine whether the remaining beam amount is sufficient for irradiating the next spot (step S812). If the remaining beam amount is sufficient ("Yes" in step S812), the interlock system 60 outputs the irradiation preparation command 612 to the timing system 50. The timing system 50 outputs the extraction condition setting timing signal 512 to the power supply controllers 45. Given the signal, the power supply controllers 45 start updating the plural extraction condition setting data items 703 (step S813). On the other hand, if it is determined in step S812 that the remaining beam amount is not sufficient, step S819 is reached.

The timing system 50 then outputs the extraction control wait timing signal 513 in time with the completion of the extraction condition setting data update, thereby terminating the update of the plural extraction condition setting data items 703 by the power supply controllers 45 and maintaining the most-recently updated values. The interlock system 60 outputs the irradiation wait command 613, and determines whether the beam extraction conditions are met on the basis of the status information 452 such as device integrity and energy stage verification information from the power supply controllers 45, the remaining beam amount measurements 152 from the remaining beam amount monitoring unit 15 in the synchrotron 13, and an extraction control permission signal 441 from the irradiation controller 44 (step S814).

If it is determined in step S814 that the conditions are not met ("NG") typically because the remaining beam amount is not sufficient for beam irradiation, the interlock system 60 outputs the irradiation stop command 614 to the timing system 50. In turn, the timing system 50 outputs the extraction condition cancellation timing signal 514 to the power supply controllers 45. Accordingly, the power supply controllers 45 update the plural extraction condition cancellation data items 704 (step S819). Upon completion of the update of the plural extraction condition cancellation data items 704, it is determined whether the extraction condition settings are abnormal (step S820).

For the moment, it is determined in step S814 that the beam extraction conditions are not met so that transition is made to extraction condition cancellation. This leads to the determination that the extraction condition settings are abnormal. The interlock system 60 then outputs the deceleration control command 616 causing the timing system 50 to output the deceleration control start timing signal 516 to the power supply controllers 45. Thereafter, having decelerated the beam, the power supply controllers 45 update the plural deceleration control data items 706 (step S821).

The timing system 50 then outputs the deceleration control end timing signal 517 in time with the completion of the deceleration control data update. The power supply controllers 45 terminate the update of the plural deceleration control data items 706 and maintain the most-recently updated values.

Next, the interlock system 60 determines whether the irradiation of all layers is completed (step S822). If it is determined that the irradiation of all layers is completed, the interlock system 60 outputs the irradiation complete command 617 to terminate the beam irradiation operation. On the other hand, if it is determined that the irradiation of all layers has yet to be completed, the interlock system 60 outputs the initial acceleration command 611 to resume the operation from initial acceleration control (step S809 is again reached for processing).

If it is determined in step S814 that the beam extraction conditions are met ("OK"), the interlock system 60 determines whether the extraction permission determination signal 355 is input on the basis of a detection signal from the affected part position detection unit 35, i.e., whether beam extraction control is to be performed (step S815).

If it is determined that beam extraction control is to be carried out given the input of the extraction permission determination signal 355 ("Yes" in step S815), the interlock system 60 outputs the beam extraction command 62 to close the radio frequency switch 21. This causes the radio frequency extraction electrode 20a to be fed with the radio frequency voltage for extraction, whereby beam extraction control is performed (step S816).

By contrast, if the extraction permission determination signal 355 is not input ("No" in step S815), then it is determined whether the extraction conditions are continuously met (step S823). If the extraction conditions are determined to be met ("OK" in step S823), control is returned to step S815, and the input of the extraction permission determination signal 355 is awaited. On the other hand, if the extraction permission determination signal 355 is not input and if the extraction conditions are not met ("NG" in step S823), the interlock system 60 outputs the irradiation stop command 614 to the timing system 50. In turn, the timing system 50 outputs the extraction condition cancellation timing signal 514 to the power supply controllers 45. The power supply controllers 45 then update the plural extraction condition cancellation data items 704 (step S819).

As described, if the extraction conditions are met ("OK" in step S814) and if the extraction conditions are continuously met ("OK" in step S823), beam extraction control is performed (step S816) provided the extraction permission determination signal is input ("Yes" in step S815). When this operation flow is adopted, beam extraction control can be performed simply and repeatedly at the same energy stage, unlike in JP-2013-111406-A involving the use of a timer that waits for the next extraction permission determination signal to be input after the input of the current extraction permission determination signal is stopped ("No" in step S815).

During beam extraction control in step S816, the dose monitor 31 attached to the irradiation apparatus 30 successively measures the dose measurement data 311 about the irradiation beam, and the irradiation controller 44 calculates the dose of each dose-managed region. With this embodiment, each dose-managed region is called a spot, and the dose with which the spot is irradiated is called the spot dose.

At this point, the irradiation controller 44 determines whether the spot dose has reached the target dose (i.e., described as the dose "attained" hereunder; step S817). If the spot dose is not attained ("No" in step S817), control is returned to step S815 and the synchrotron 13 continuously performs beam extraction control (steps S815, S816 and S823). On the other hand, if the spot dose is attained ("Yes" in step S817), it is determined whether all spot doses constituting the radiation range at the current energy stage (called the intra-layer dose hereunder) are attained (step S818).

If the intra-layer dose is not attained ("No" in step S818), it is determined whether the remaining beam amount is sufficient for irradiating the next spot (step S824). If it is determined that the remaining beam amount is sufficient ("Yes" in step S824), the irradiation controller 44 changes the beam irradiation position by changing the excitation amount of a scanning magnet 32 (step S825) and irradiates the next spot continuously. On the other hand, if it is determined that the remaining beam amount is not sufficient, step S819 is reached. The interlock system 60 outputs the irradiation stop command 614 to the timing system 50. The timing system 50 outputs the extraction condition cancellation timing signal 514 to the power supply controllers 45. In turn, the power supply controllers 45 update the plural extraction condition cancellation data items 704 (step S819).

If it is determined in step S817 that the intra-layer dose is attained ("Yes"), the interlock system 60 outputs the irradiation stop command 614 to the timing system 50 so as to irradiate the next layer. The timing system 50 outputs the extraction condition cancellation timing signal 514 to the power supply controllers 45. In turn, the power supply controllers 45 update the plural extraction condition cancellation data items 704 (step S819). It is then determined whether the extraction condition settings are abnormal (step S820). Because the transition in this case to extraction condition cancellation is not triggered by an anomaly in the extraction condition settings ("No"), the interlock system 60 first determines whether the next target energy data exists (step S830). If the next target energy data is determined to exist, then it is determined whether the remaining beam amount is sufficient for irradiation of the next spot (step S826). On the other hand, if it is determined in step S830 that the next target energy data does not exist, i.e., that the irradiation of all layers is completed, the interlock system 60 outputs the irradiation complete command 617 to terminate the beam irradiation operation. Alternatively, step S830 may be interposed between step S819 and step S820.

If it is determined in step S826 that the remaining beam amount is sufficient ("Yes"), the interlock system 60 outputs the energy change command 615 to the timing system 50. The timing system 50 outputs the energy change control timing signal 515 to the power supply controllers 45. On the other hand, if it is determined in step S826 that the remaining beam amount is not sufficient ("No"), the interlock system 60 outputs the deceleration control command 616 and goes to step S821.

The power supply controllers 45 then update the energy change data items 705 (step S827).

At the end of the energy change, the accelerator controller 40 outputs the beam energy information 402 to the interlock system 60. The interlock system 60 determines whether the energy stage reached after the energy change matches the target energy stage on the basis of the beam energy information 402 sent from the accelerator controller 40 (step S828).

If it is determined in step S828 that the energy stage reached upon completion of the energy change matches the target energy stage ("Yes"), the interlock system 60 outputs the irradiation preparation command 612 to the timing system 50. The timing system 50 outputs the extraction condition setting timing signal 512 to the power supply controllers 45. In turn, the power supply controllers 45 start updating the plural extraction condition setting data items 703 (step S813).

On the other hand, if it is determined in step S828 that the energy stage reached upon completion of the energy change does not match the target energy stage, the interlock system 60 again outputs the energy change command 615 to the timing system 50. The timing system 50 outputs the energy change control timing signal 515 to the power supply controllers 45. In turn, the power supply controllers 45 update the plural energy change control data items 705 (step S827).

After repeating the above-described control (steps S813 through S820), the interlock system 60 outputs the deceleration control command 616 to the timing system 50. The timing system 50 outputs the deceleration control start timing signal 516 to the power supply controllers 45. In turn, the power supply controllers 45 start updating the plural deceleration control data items 706 (step S821).

Upon completion of the deceleration control data update, it is determined whether the irradiation of all layers is completed (step S822). If it is determined that the irradiation of all layers is complete ("Yes" in step S822), the operation control of the synchrotron 13 is terminated. If there exists a layer that has yet to be irradiated, the interlock system 60 changes the target energy stage after verifying that the equipment is operating normally, and outputs the initial acceleration command 611 (the processing is again performed starting from step S809).

FIGS. 7A and 7B depict examples of the control data being output during the multistage extraction operation characteristic of this embodiment. Shown in FIGS. 7A and 7B are the output examples involving the use of the output operation control data items 70 indicated in FIG. 3. Three stages of energy Ea, Eb and Ec can be extracted in one operation cycle.

FIG. 7A shows changes in the exciting current of the bending magnet in effect when the ion beam at three energy stages (Ea, Eb and Ec) is subjected to extraction control in one operation cycle. FIG. 7B shows changes in the exciting current of the bending magnet in effect when, after the extraction of an ion beam at two energy stages (Ea, Eb) in the initial operation cycle, an exhausted remaining ion beam amount triggers transition to deceleration control which updates the operation cycle, so that an ion beam at the third energy stage (Ec) is extracted in the next operation cycle.

Generally, the exciting current of the bending magnet is approximately proportional to the beam energy. It follows that what is shown in FIGS. 7A and 7B may also be interpreted as changes in beam energy during the multistage extraction operation.

What is common to FIGS. 7A and 7B is that the timing signals 511 through 517 are set corresponding to the control data items 701 through 706. The control data items 701 through 706 are updated on the basis of the timing signals 511 through 517 being input.

First, the output example of multistage extraction control is explained with reference to FIG. 7A.

When the acceleration control start timing signal 511 is input from the timing system 50, the power supply controllers 45 select the initial acceleration control data item 701 and start exciting current data update control.

Upon completion of initial acceleration control, the timing system 50 inputs the extraction condition setting timing signal 512 to the power supply controllers 45. The power supply controllers 45 output the plural extraction condition setting data items 703a corresponding to the initial extraction energy stage Ea.

Thereafter, upon input of the extraction control wait timing signal 513, the power supply controllers 45 maintain the most-recently updated values and carry out extraction control.

Upon completion of extraction control, the timing system 50 outputs the extraction condition cancellation timing signal 514 to the power supply controllers 45. In turn, the power supply controllers 45 start updating and outputting the plural extraction condition cancellation data items 704a.

Upon completion of the update control the plural extraction condition cancellation data items 704a, the remaining beam amount inside the synchrotron 13 is measured. After determining that the remaining beam amount is sufficient for beam extraction at the next energy stage, the timing system 50 outputs the energy change control timing signal 515. The power supply controllers 45 select the plural energy change control data items 705ab that connect the current extraction energy stage Ea with the next extraction energy stage Eb, and start updating and outputting the control data.

Thereafter, the above-described extraction condition setting control, extraction control, extraction condition cancellation control, and energy change control are repeated until the extraction control of the last energy stage Ec is completed.

Upon completion of the update control of the extraction condition cancellation data item 704c at the last energy stage Ec, the timing system 50 outputs the deceleration control start timing signal 516. Given the input of the deceleration control start timing signal 516, the power supply controllers 45 select the deceleration control data item 706c corresponding to the preceding extraction condition cancellation data item 704c, and start updating and outputting the deceleration control data.

Incidentally, since this embodiment performs beam extraction control at the energy stages ranging progressively from low to high (Ea<Eb<Ec), the embodiment carries out initial excitation up to a maximum energy stage (Einit) during deceleration control.

In time with the completion of deceleration control, the timing system 50 outputs the deceleration control end timing signal 517 and determines whether extraction control at all energy stages is completed. If it is determined that extraction control is complete at all energy stages, the operation cycle of the synchrotron is terminated.

Explained next is the case where the operation cycle is updated during the multistage extraction operation as shown in FIG. 7B. The reference characters in FIG. 7B are the same as those in FIG. 7A. The explanation below applies following the end of extraction control at the second energy stage Eb in FIG. 7B.

Upon completion of extraction control at the second energy stage Eb, the remaining beam amount inside the synchrotron 13 is measured. If the result of the measurement reveals that due to beam exhaustion in particular, the remaining beam amount inside the synchrotron 13 is not sufficient for the next stage of beam extraction, the timing system 50 outputs the deceleration control start timing signal 516 corresponding to the energy stage at which extraction control has ended. On the basis of the deceleration control start timing signal 516 being input, the power supply controllers 45 start the update control of the deceleration control data item 706b that can connect continuously with the preceding extraction condition cancellation data item 704b.

In time with the input of the deceleration control end timing signal 517, it is determined whether extraction control at all energy stages is completed. If it is determined that extraction control at all energy stages has yet to be complete, the acceleration control start timing signal 511 is again output following the change of the target energy stage from Eb to Ec.

Given the input of the acceleration control start timing signal 511, the update of the initial acceleration control data item 701 is started. Upon completion of initial acceleration control, a comparison is made between the energy stage reached and the target energy stage. In this case, the beam needs to be further accelerated because the reached energy stage of the initial acceleration control data item 701 is Ea and the target energy stage is Ec. Thus the energy change control timing signal 515 is output. On the basis of the energy change control timing signal 515, the power supply controllers 45 perform energy change control by updating the plural energy change control data items 705ab. At the end of energy change control, a comparison is again made between the energy stage reached and the target energy stage. Because the energy stage reached after energy change control is Eb and the target energy stage is Ec, the energy change control timing signal 515 is again output and the plural energy change control data items 705bc are updated accordingly. This control is repeated until the reached energy stage becomes equal to the target energy stage Ec through acceleration. Thereafter, the above-described extraction control and deceleration control are carried out in the same manner.

As will be discussed later with reference to FIGS. 8(d) and 8(e), during acceleration up to the energy stage Ec, the beam may be accelerated by use of the initial acceleration control data item for direct acceleration from the energy stage Einj to the stage Ec. This further shortens the time required for acceleration, so that the dose rate is further improved and treatment time is shortened accordingly.

FIG. 8 is a set of diagrams showing an example of the control data being output for irradiation of a respiratory moving organ during the multistage extraction operation characteristic of this embodiment. In FIG. 8, as in FIGS. 7A and 7B, the output example involving the use of the operation control data 70 shown in FIG. 3 is depicted. The case of FIG. 8 aims irradiating the respiratory moving organ at six energy stages (Ea through Ef). With this embodiment, up to three stages of energy are assumed to be extracted in one operation cycle, with the operation control data 70 formed by the data items 70ac for irradiation with the beam at the energy stages Ea, Eb and Ec and by the data items 70df for irradiation with the beam at the energy stages Ed, Ee and Ef.

FIG. 8(a) shows time changes of an affected part position detection signal observed by the affected part position detection unit 35. FIG. 8(b) shows how the extraction permission determination signal 355 is output. The extraction permission determination signal 355 in FIG. 8(b) is output in such a manner that the affected part is irradiated only when positioned in regions where the change of the affected part is stable (i.e., below the dotted straight line in FIG. 8(a)), whereby the affected part 37 is accurately irradiated.

FIG. 8(c) shows the beam extraction command 62 output from the interlock system 60. The beam extraction command 62 is output on the basis of the extraction condition setting state of the synchrotron 13 and the extraction permission determination signal 355.

FIG. 8(d) shows the operation control data items 70ac and 70df about the bending magnet 18 making up part of the synchrotron 13. FIG. 8(e) shows the operation control data items 70ac and 70df regarding the quadrupole magnet 19 constituting part of the synchrotron. Unlike the operation control data items about the bending magnet 18 in FIG. 8(d), the operation control data items regarding the quadrupole magnet 19 in FIG. 8(e) have the excitation amounts changed in the extraction condition setting data 703 and extraction condition cancellation data 704 because of the need for making transition from the operation conditions upon acceleration control of the synchrotron 13 to the operation conditions at the time of extraction control.

In this case, the regions where beam extraction control is available with the synchrotron 13 are found in segments indicated by dotted lines in FIGS. 8(d) and 8(e), each of the segments ranging from the extraction control wait timing signal 513 to the extraction condition cancellation timing signal 514.

A method for outputting the beam extraction command 62 shown in FIG. 8(c) is now explained. The beam extraction command 62 is determined by the four conditions described below.

The conditions are made up of four types of regions: regions (901 (901a, 901b, 901c, 901d, . . . )) where the extraction permission determination signal 355 is ON outside the segment between the extraction control wait timing signal 513 and the extraction condition cancellation timing signal 514; regions (902 (902a, 902b, . . . )) where the extraction permission determination signal 355 is OFF inside the segment between the extraction control wait timing signal 513 and the extraction condition cancellation timing signal 514; regions (903 (903a, 903b, . . . )) where the extraction permission determination signal 355 is OFF outside the segment between the extraction control wait timing signal 513 and the extraction condition cancellation timing signal 514; and regions (904 (904*a*, 904*b*, 904*c*, ... )) where the extraction permission determination signal 355 is ON inside the segment between the extraction control wait timing signal 513 and the extraction condition cancellation timing signal 514.

The beam extraction command 62 (beam ON) is output only in the regions (904) where the extraction permission determination signal 355 is ON inside the segment between the extraction control wait timing signal 513 and the extraction condition cancellation timing signal 514.

Explained below with reference to the timing chart in FIG. 8 is how the beam extraction command 62 is output.

First, a beam at an injection energy stage Einj is injected into the synchrotron 13, and the initial acceleration data item 701 is updated. With the initial acceleration data item updated, the beam energy reaches the stage Ea, and the plural extraction condition setting data items 703 are updated. The beam extraction command 62 remains OFF until after the update of the plural extraction condition setting data items 703 is completed (901*a*).

After the update of the extraction condition setting data is cancelled, the beam extraction command 62 is turned ON only in the region where the extraction permission determination signal 355 remains ON (904*a*). At this point, with the extraction permission determination signal 355 turned OFF, if the remaining beam amount inside the synchrotron 13 is sufficient and if the equipment is normally operating, the synchrotron 13 enters the standby state (902*a*) because the control of beam extraction from the synchrotron 13 is available. The extraction permission determination signal 355 is again turned ON, and the beam extraction command 62 is turned ON (904*b*).

When the control flow shown in FIG. 6 is followed as described above, beam extraction control can be performed a number of times on the basis of the extraction permission determination signal 355 in the regions where the synchrotron 13 is inside the segment between the extraction control wait timing signal 513 and the extraction condition cancellation timing signal 514.

When the dose of the current layer is attained, the extraction conditions are cancelled, the energy stage is changed, and the extraction conditions are set so as to change to the beam energy stage Eb corresponding to the next layer.

As shown in FIG. 8(*e*), the excitation amount of the quadrupole magnet 18 is changed successively during extraction condition cancellation, energy change, and extraction condition setting. This allows the multistage extraction control operation to be implemented efficiently without incurring beam loss.

In the segment between extraction condition cancellation and extraction condition setting, the control of beam extraction from the synchrotron cannot be performed. Thus in this segment, the beam extraction command 62 is turned OFF even if the extraction permission determination signal 355 is ON (901*b*) as shown in FIG. 8(*a*).

Upon completion of the change of the energy stage and the setting of the extraction conditions on the synchrotron 13, the beam extraction command 62 is turned ON in the region where the extraction permission determination signal 355 is ON (904*c*).

At this point, if there occurs a momentary change in the position of the affected part observed by the affected part position detection unit 35 typically as a result of the patient's physiological activities (353*a* in FIG. 8(*a*)), the extraction permission determination signal 355 is turned OFF momentarily. Thereafter, when the position of the affected part 37 returns to the beam irradiation permission range 353, the extraction permission determination signal 355 is turned ON, and the beam extraction command 62 is changed in synchronization (902*b* to 904*d*).

When the control flow shown in FIG. 6 is followed in the manner described above, beam irradiation is carried out safely even if the position of the affected part is momentarily changed due to the patient's physiological activities.

Thereafter, the control of beam energy change from the stage Eb to the stage Ec is performed (903*a*), and the beam extraction command 62 is again turned ON (904*e*).

With this embodiment, it is assumed that beam extraction control indicated at 904*e* has caused the dose of the currently irradiated layer to be attained and that the remaining beam amount is not sufficient for beam irradiation at the next energy stage. The extraction conditions are thus cancelled (704*c*) and deceleration control is performed (706*c*).

Thereafter, the beam is accelerated (701*d*) under initial acceleration control from the injection energy stage Einj to the stage Ed in carrying out irradiation at the next energy stage Ed, and the extraction conditions are set (703*d*). During this time, the output of the beam extraction command 62 remains OFF (901*c*). Upon completion of the setting of the extraction conditions and at the time the extraction permission determination signal 355 is input, the beam extraction command 62 is again turned ON (904*f*). After this, irradiation is performed likewise with the beam energy changed to the energy stage Ee, followed by irradiation and deceleration controlled at the beam energy stage Ef.

When the remaining beam amount is not sufficient at the beam energy stage Eb, Ed, Ee or Ef, the same deceleration and the acceleration control from the stage Ec to the stage Ed as discussed above are carried out.

Whereas the initial acceleration control data item 701*d* is used to accelerate the beam energy directly from the injection energy stage Einj to the stage Ed, the beam energy may be accelerated alternatively as shown in FIG. 7B by resorting to the combination of direct acceleration from the injection energy stage Einj to the stage Ea using the initial acceleration control data item 701*a*, acceleration from Ea to Eb (705*ab*), acceleration from Eb to Ec (705*bc*), and acceleration from Ec to Ed. Still, as depicted in FIG. 8, it takes less time to accelerate the beam energy directly from the injection energy stage Einj to the stage Ed.

According to this embodiment described above, the equipment and control arrangements (control system 100) making up the synchrotron 13 include: units (power supply controllers 45) for selectively updating the operation control data items 70 for output to the power supply 46; a unit (timing system 50) for controlling beam extraction from the synchrotron 13; units (remaining beam amount monitoring unit 15 and remaining beam amount measurement unit 151) for detecting the amount of the beam circulating inside the synchrotron 13; a unit (dose monitor 31) for detecting the dose with which the affected part 37 is irradiated; a unit (irradiation controller 44) for obtaining the remaining irradiation dose from the target dose with which to irradiate the affected part 37 and from the dose with which the affected part 37 has been actually irradiated; units (affected part position detection unit 35 and transparent image acquisition unit 351) for detecting movements of the affected part 37 caused by the physiological activities of the patient 36; a unit (extraction permission determination unit 354) for outputting the extraction permission determination signal 355 on the basis of the values output from the units detecting the movements of the affected part 37; and a unit (interlock system 60) for switching the operation control of the synchrotron 13 on the basis of the extraction permission determination signal 355, the remaining beam amount detected inside the synchrotron 13, the remaining dose with which to irradiate the affected part, and the irradiation completion signal 445 indicating that the control of beam extraction from the synchrotron 13 is available.

For the multistage extraction control operation whereby the control of extraction beam energy change on the synchrotron is performed in a short time, the control data 701 through 706 are arranged to have the plural deceleration control data items 706 corresponding to the plural energy stages so that transition can be made rapidly to deceleration control from any energy stage. This makes it possible to perform in a short time the update of the operation cycle when ion beam irradiation is interrupted due to an insufficient remaining beam amount inside the synchrotron, whereby the dose rate is improved and treatment time is shortened.

Also, if a failure in the component devices making up the charged particle beam irradiation system has interrupted ion beam irradiation, direct transition can be made from the extraction energy to deceleration control, so that the operation cycle is updated safely and in a short time.

Further, where there remains an energy stage at which beam irradiation has yet to be performed and the operation cycle is to be updated after deceleration control is terminated typically because of an exhausted beam having interrupted beam irradiation, if the energy stage reached upon completion of initial acceleration control or energy change control does not match the next target energy stage, then energy change control is carried out immediately to accelerate the currently reached energy stage up to the target energy stage without executing the control of the extraction control data update (extraction condition setting control and extraction condition cancellation control). This contributes to performing energy change control in a short time, whereby the dose rate is improved and treatment time is shortened.

The control data items 701 through 706 making up the operation control data are structured by use of current/voltage time-series data as controlled variables given directly to the component devices constituting the synchrotron 13. This eliminates the need for performing calculations to change parameters, so that the equipment configuration and control device arrangements are simplified.

Also, the data storage device 42 stores as module data the control data items permitting beam extraction at all energy stages corresponding to the irradiation conditions of all predictable patients. The main controller 41 selects the control data items 701 through 706 on the basis of the irradiation conditions 421 and stores the selected data items into the power supply controllers 45 to constitute the operation control data 70. This eliminates the wasteful time that does not contribute to beam irradiation (control time ranging from injection beam energy to irradiation start energy on the synchrotron 13, and control time ranging from irradiation end energy to deceleration end energy). As a result, beam irradiation over the desired energy range can be performed in a short operation cycle, so that the dose rate is improved and treatment time is shortened.

Furthermore, when control is implemented in accordance with the control flow shown in FIG. 6, it is possible to carry out beam irradiation stably corresponding to the movements of respiratory moving organs during the multistage extraction control operation.

It should be understood that the present invention when embodied is not limited to the above-described embodiment and that various modifications, variations and alternatives may be made of the invention so far as they are within the spirit and scope of the appended claims. The embodiment is given as a detailed, comprehensive explanation of the present invention. The invention is thus not limited to any embodiment containing all components explained above.

For example, the method for detecting the affected part 37 was described above as one of detecting the marker 352. Alternatively, the affected part 37 may be detected directly. Some other suitable known method may also be adopted for the purpose.

Thus the scope of the invention should be determined by the appended claims and their legal equivalents, rather than by the examples given.

What is claimed is:

1. A charged particle beam irradiation system comprising:
   a synchrotron accelerating an ion beam and having the accelerated ion beam extracted therefrom;
   an irradiation device for executing irradiation with the ion beam extracted from the synchrotron;
   a detection means for detecting a movement of an affected part of a patient caused by physiological activities of the patient;
   an extraction permission determination means for outputting an extraction permission determination signal on the basis of an output value from the detection means; and
   a controller for causing operation control data about component devices making up the synchrotron to be formed by at least one initial acceleration control data item, a plural extraction control data items for ion beam extraction at a plural energy stages, a plural energy change control data items connecting the plural extraction control data items, and a plural deceleration control data items corresponding to the plural extraction control data items, the controller further combining the control data items to provide beam extraction control at a plural energy stages, wherein
   the controller performs control of beam extraction from the synchrotron on the basis of the extraction permission determination signal output from the extraction permission determination means.

2. The charged particle beam irradiation system according to claim 1, wherein, upon control of extraction of the beam from the synchrotron, the controller performs control of beam extraction a plural times at the same energy stage on the basis of the extraction permission determination signal output from the extraction permission determination means.

3. The charged particle beam irradiation system according to claim 2, wherein the extraction permission determination means outputs the extraction permission determination signal if the detection means detects that the affected part is within an extraction permission range, the extraction permission determination means not outputting the extraction permission determination signal if the detection means detects that the affected part is not within the extraction permission range.

4. The charged particle beam irradiation system according to claim 1, wherein the controller includes:
   a timing system for outputting a plural control timing signals for managing control timings of the component devices making up the synchrotron; and
   a power supply controller for controlling the component devices making up the synchrotron, wherein
   the initial acceleration control data item, the plural extraction control data items, the plural energy change control data items, and the plural deceleration control data items forming the operation control data are stored in the power supply controller, and
   the power supply controller inputs the plural control timing signals output from the timing system and, on the basis of the plural control timing signals, updates selectively the initial acceleration control data item, the plural extraction control data items, the plural energy change control data items, and the plural deceleration control data items.

5. The charged particle beam irradiation system according to claim 4, further comprising a beam amount detection means for detecting the amount of the beam accumulated in the synchrotron, wherein given the input of the extraction permission determination signal output from the extraction permission determination means, the controller sets extraction conditions for operation control of the synchrotron, the controller further issuing a command to perform beam extraction control upon input of the extraction permission determination signal, and if the extraction permission determination signal is stopped, the controller determines whether to wait to permit beam extraction at the current energy stage when the extraction permission determination signal is again output, to make transition to energy change control so as to permit beam irradiation at the next energy stage, or to make transition to deceleration control in accordance with the detected amount of the beam accumulated in the synchrotron and with the result of a determination of whether beam irradiation at the current energy stage has been completed, the controller further outputting to the timing system a control command corresponding to the control determined earlier.

6. The charged particle beam irradiation system according to claim 4, wherein the controller further includes an interlock system that outputs an initial acceleration command to accelerate beam energy injected into the synchrotron up to an initial extraction energy stage for beam extraction, an irradiation preparation start command to set extraction conditions following initial acceleration or energy change with the synchrotron, an irradiation wait command to indicate that the setting of the extraction conditions is completed on the synchrotron, a beam extraction command to be output in accordance with the extraction permission determination signal output from the extraction permission determination means and with status of the extraction conditions set on the synchrotron, an irradiation stop command to stop beam irradiation aimed at the affected part, an energy change command to be output on the basis of irradiation progress information about the ion beam with which the patient has been irradiated, a deceleration control command to be output on the basis of status of the component devices making up the charged particle beam irradiation system including the synchrotron and the irradiation device, and an irradiation complete command to indicate that the irradiation is completed, and the timing system selectively outputs the corresponding one of the plural control timing signals on the basis of the initial acceleration command, the irradiation preparation start command, the irradiation wait command, the irradiation stop command, the energy change command, and the deceleration control command output from the interlock system.

7. The charged particle beam irradiation system according to claim 6, wherein the interlock system further outputs the deceleration control command if a failure has occurred in any one of the component devices making up the charged particle beam irradiation system including the synchrotron and the irradiation device, and upon input of the timing signal for starting deceleration control from the timing system, the power supply controller first updates the current control data and then selects one of the plural deceleration control data items which corresponds to the energy stage reached upon completion of update control so as to make transition to deceleration control.

8. The charged particle beam irradiation system according to claim 6, wherein the interlock system outputs the energy change command if the next target energy stage exists upon completion of extraction control at a given energy stage or if the energy stage reached upon completion of initial acceleration control or upon completion of energy change control does not match the next target energy stage, upon input of the energy change command, the timing system selectively outputs the timing signal for energy change control from among the plural control timing signals, and upon input of the timing signal for energy change control, the power supply controller selects one of the plural energy change control data items which corresponds to the given energy stage or to the reached energy stage to perform control so as to make transition to energy change control.

9. The charged particle beam irradiation system according to claim 4, wherein, given the timing signal for starting deceleration control from among the timing signals input from the timing system, the power supply controller selects one of the plural deceleration control data items which corresponds to the energy stage in effect upon completion of irradiation control, the power supply controller further performing control to make transition to deceleration control.

10. The charged particle beam irradiation system according to claim 1, wherein the initial acceleration control data item, the plural extraction control data items, the plural energy change control data items, and the plural deceleration control data items are formed by current/voltage time-series data as controlled variables given directly to the component devices making up the synchrotron.

11. The charged particle beam irradiation system according to claim 1, wherein the controller includes:

a data storage device for storing as module data the control data including the initial acceleration control data item, the plural extraction control data items, the plural energy change control data items, and the plural deceleration control data items for permitting beam extraction at all energy stages corresponding to irradiation conditions for a plural predictable patients; and a power supply controller for controlling the component devices making up the synchrotron, wherein given the irradiation conditions of a specific patent preparatory to irradiation, the controller selects the applicable control data items from among the module data stored in the data storage device and stores the selected data items into the power supply controller so as to constitute the operation control data.

12. A charged particle beam irradiation system comprising:

a synchrotron accelerating an ion beam and having the accelerated ion beam extracted therefrom;

an irradiation device for executing irradiation with the ion beam extracted from the synchrotron;

a detection means for detecting a movement of an affected part of a patient caused by physiological activities of the patient;

an extraction permission determination means for outputting an extraction permission determination signal on the basis of an output value from the detection means;

a data storage device for storing, as module data, control data items for permitting beam extraction at all energy stages corresponding to irradiation conditions for a plural predictable patients, the control data items including at least one initial acceleration control data item, a plural extraction control data items, a plural energy change control data items, and a plural deceleration control data items corresponding to the ion beam at a plural energy stages;

a power supply controller for controlling component devices making up the synchrotron; and a controller which, given the irradiation conditions of a specific patent preparatory to irradiation, selects the applicable control data items from among the module data stored in the data storage device and stores the selected data items into the power supply controller so as to constitute the operation control data about the devices making up the synchrotron, wherein the controller performs control of beam extraction from the synchrotron on the basis of the extraction permission determination signal output from the extraction permission determination means.

13. A method for operating a charged particle beam irradiation system including a synchrotron accelerating an ion beam and having the accelerated ion beam extracted therefrom;

an irradiation device for executing irradiation with the ion beam extracted from the synchrotron;

a detection means for detecting a movement of an affected part of a patient caused by physiological activities of the patient; and an extraction permission determination means for outputting an extraction permission determination signal on the basis of an output value from the detection means, the method comprising:

causing operation control data about component devices making up the synchrotron to be formed by an initial acceleration control data item, a plural extraction control data items for ion beam extraction at a plural energy stages, a plural energy change control data items connecting the plural extraction control data items, and a plural deceleration control data items corresponding to the plural extraction control data items;

combining the control data items to provide beam extraction control at the plural energy stages;

permitting rapid transition to deceleration control from any energy stage by use of the plural deceleration control data items corresponding to the plural energy stages; and performing control of beam extraction from the synchrotron on the basis of the extraction permission determination signal output from the extraction permission determination means.

14. The method for operating the charged particle beam irradiation system according to claim 13, wherein:

preparing as module data the control data items for permitting beam extraction at all energy stages corresponding to irradiation conditions for a plural predictable patients, the control data items including the initial acceleration control data item, the plural extraction control data items, the plural energy change control data items, and the plural deceleration control data items constituting the operation control data; and given the irradiation conditions of a specific patent, selecting the applicable control data items from among the module data so as to constitute the operation control data.

\* \* \* \* \*